United States Patent [19]

Rother et al.

[11] Patent Number: 5,847,082

[45] Date of Patent: Dec. 8, 1998

[54] TERMINAL COMPLEMENT INHIBITOR FUSION PROTEINS

[75] Inventors: Russell Rother, Cheshire; Scott Rollins, Monroe; Stephen P. Squinto, Bethany, all of Conn.

[73] Assignee: Alexion Pharmaceuticals, Inc., New Haven, Conn.

[21] Appl. No.: 482,148

[22] Filed: Jun. 7, 1995

Related U.S. Application Data

[62] Division of Ser. No. 205,720, Mar. 3, 1994, abandoned.

[51] Int. Cl.$^6$ .......................... C07K 14/435; C12N 15/62
[52] U.S. Cl. ........................................... 530/350; 435/69.7
[58] Field of Search ............................. 530/350; 435/69.7

[56] References Cited

U.S. PATENT DOCUMENTS

| | | | |
|---|---|---|---|
| 5,521,066 | 5/1996 | Menzel et al. | 435/7.2 |
| 5,550,108 | 8/1996 | Sims et al. | . |
| 5,573,940 | 11/1996 | Sims et al. | 435/240.2 |
| 5,624,837 | 4/1997 | Fodor et al. | . |
| 5,627,264 | 5/1997 | Fodor et al. | . |
| 5,660,825 | 8/1997 | Sims et al. | . |
| 5,705,732 | 1/1998 | Sims et al. | . |

OTHER PUBLICATIONS

Su et al J. Cell Biol. vol. 112 (3) pp.377–384, Feb. 1991.
Albrecht, et al., 1992. "Herpesvirus Saimiri Has a Gene Specifying a Homologue of the Cellular Membrane Glycoprotein CD59" *Virology* 190:527–530.
Brown, et al., 1992. "Sorting of GPI–Anchored Proteins to Glycolipid– Enriched Membrane Subdomains during Transport to the Apical Cell Surface" *Cell.* 68:533–544.
Butikofer, et al., 1989. "Enrichment of Two Glycosyl–Phosphatidylinositol–Anchored Proteins, Acetylcholinesterase and Decay Accelerating Factor, in Vesicles Released form Human Red Blood Cells" *Blood.* 74:1481–1485.
Cinek, et al., 1992. "The nature of large noncovalent complexes containing glycosylphosphatidylinositol–anchored membrane glycoproteins and protein tyrosine kinases" *J. Immunol.* 149:2262–2270.
Davies, et al., 1989. "CD59, an LY–6–like protein expressed in human lymphoid cells, regulates the action of the complement membrane attack complex on homologous cells" *J. Exp. Med.* 170:637–654.
Ferguson, et al., 1988. "Cell–Surface Anchoring of Proteins via Glycosyl–Phosphatidylinositol Structure" *Ann. Rev. Biochem.*, 57:285–320.
Holguin, et al., 1989. "Isolation and characterization of a membrane protein from normal human erythrocytes that inhibits reactive lysis of the erythrocytes that inhibits reactive lysis of the erythrocytes of paroxysmal nocturnal hemoglobinuria" *J. Clin. Invest.* 84:7–17.
Lublin, et al., 1991. "Phospholipid–anchored and Transmembrane Versions of Either Decay–Accelerating Factor or Membrane Cofactor Protein Show Equal Efficiency in Protection from Complement–mediated Cell Damage" *J. Exp. Med.*, 174:35–44.

McMahon, et al., 1989. "Ectopic Expression of the Proto–Oncogene int–1 in Xenopus Embryos Leads to Duplication of he Embryonic Axis" *Cell.* 58:1075–1084.
Meri, et al., 1990. "Human protection (CD59), an 18,000–20,000 MW complement lysis restricting factor, inhibits C5b–8 catalysed insertion of C9 into lipid bilayers" *Immunology* 71:1–9.
Moran, et al., 1992. "Human recombinant soluble decay accelerating factor inhibits complement activation in vitro and in vivo" *J. Immunol.* 140:1736–1743.
Nakano, et al., 1993. "Expressions and Characterizations of Recompinant MACIFs (CD59) of Three Different Lengths" *Molec. Immunol.* 30(suppl. 1):37.
Norris, et al., 1993. "Structure–Function Relationships of CD59" *Blood*, 82(suppl.):202a.
Okada, et al., 1989. "Monoclonal Antibodies Capable of Causing Hemolysis Of Neuraminidase–Treated Human Erythrocytes by Homologus Complement" *J. Immunol.* 143:2262–2266.
Okada, et al., 1989. "20 KDa Homologous Restriction Factor of Complement Resembles T Cell Activating Protein" *Biochem. Biophys. Res. Commun.* 162: 1553–1559.
Petranka, et al., 1993. "The Structure and Function fo CD59: The Importance of the Disulfide Structure and Identification of a Primary Epitope" *Molec. Immunol.* 30(suppl. 1):44.
Philbrick, et al., 1990. "The CD59 Antigen Is A Structural Homologue of Murine Ly–6 Antigens but Lacks Interferon Inducibility" *Eur. J. Immunol.* 20:87–92.
Purcell, et al., 1991. "Alternatively Spliced RNAs Encode Several Isoforms of CD46 (MCP), A Regulator of Complement Activation" *Immunogenetics* 33:335–344.
Rollins, et al., 1990. "The Complement–Inhibitory Activity of Cd59 Resides in its Capacity to Block Incorporation of C9 into Membrane C5b–9" *J. Immunol.* 144:3478–3483.
Rollins, et al., 1991. "Inhibition of Homologous Complement by CD59 is Mediated by A Species–Selective Recognition Conferred Through Binding to C8 within C5b–8 or C9 within C5b–9" *J. Immunol.* 146:2345–2351.
Rother, et al., 1994. "Inhibition of Complememt–Mediated Cytolysis by the terminal Complement Inhibitor of Herpesvirus Saimiri" *J. Virol.* 68:730–737.

(List continued on next page.)

*Primary Examiner*—David L. Fitzgerald
*Assistant Examiner*—Daryl A. Bagham
*Attorney, Agent, or Firm*—Seth A. Fidel, Ph.D.; Maurice M. Klee

[57] ABSTRACT

Nucleic acid sequences encoding chimeric proteins that comprise a functional portion of a parent terminal complement inhibitor, such as CD59, and a heterologous transmembrane domain are provided. The parent terminal complement inhibitor is modified to inactivate its GPI signal sequence. The heterologous transmembrane domain serves to anchor the chimeric protein to the cell membrane without substantially interfering with the complement inhibitor activity of the terminal complement inhibitor. The nucleic acid sequences and encoded chimeric proteins can be used to protect cells from complement attack.

4 Claims, 6 Drawing Sheets

OTHER PUBLICATIONS

Sawada, et al., 1990. "Isolation and Expression of the Full–Length cDNA Encoding CD59 Antigen of Human Lymphocytes" *DNA and Cell. Biol.* 9:213–220.

Seaman, et al., 1991. "Molecular Cloning of gp42, a Cell–Surface Molecle That Is Selectively Induced on Rat Natural Killer Cells by Interleukin 2: Glycolipid Membrane Anchoring and Capacity for Transmembrane Signaling" *J. Exp. Med.* 173:251–260.

Stefanova, et al., 1989. "Characterization of a Broadly Expressed Human Leucocyte Surface Antigen MEM–43 Anchored in Membrane Through Phosphatidylinositol" *Mol. Immunol.* 26:153–161.

Su, et al., 1991. "The Glycolsyl Phosphatidylinositol Anchor Is Critical for Ly–6A/E–Mediated T Cell Activation" *J. Cell Biol.* 112:377–384.

Suter, et al., 1992. "NGF/BDNF Chimeric Proteins: Analysis of Neurotrophin Specificity by Homolog–scanning Mutagenesis" *J. Neurosci.* 12:306–318.

Tone, et al., 1992. "Gene Structure of Human CD59 and Demonstration that Discrete mRNAs Are Generated by Alternative Polyadenylation" *J. Mol. Biol.* 227:971–976.

Venneker, et al., 1992. "CD59: A Molecule Involved in Antigen Presentation as well as Downregulation of Membrane Attack Complex" *Exp. Clin. Immunogenet.* 9:33–47.

Walsh, et al., 1991. "Transfection of Human CD59 Complementary DNA into Rat Cells Confers Resistance to Human Complement" *Eur. J. Immunol.* 21:847–850.

Whitlow, et al., 1991. "H19, a Surface Membrane Molecule Involved in T–Cell Activation, Inhibits Channel Formation by Human Complement" *Cell Immunol.* 126:176–184.

Whitlow, et al., 1993. "Cells Lacking Glycan Phosphatidylinositol–Linked Proteins Have Impaired Ability to Vesiculate" *Blood.* 81:510–516.

Wing, et al., 1992. "Oligodendrocytes Lack Glycolipid Anchored Proteins which Protect them against Complement Lysis by Incorporation of CD59" *Immunology.* 76:140–145.

Zalman, et al., 1986. "Isolation of a Human Erythrocyte Memebrane Protein Capable of Inhibiting Expression of Homologous Complemennt Transmembrane Channels" *Proc. Natl. Acad. Sci. USA.* 83:6975–6979.

Zhao, et al., 1991. "Amplified Gene Expression in CD59–Transfected Chinese Hamster Ovary Cells Confers Protection against the Membrane Attack Complex of Human Complement" *J. Biol. Chem.* 266:13418–13422.

Lehto, et al., 1993. "Interactions of Soluble CD59 with the Terminal Complement Complexes: CD59 and C9 Compete for A Nascent Epitope on C8" *J. Immunol.* 151:4941–4949.

Okada et al., 1990. "Erythrocytes of Patients with Paroxysmal Nocturnal Haemoglobinuria Acquire Resistance to Complement Attack by a Purified 20–kD Homologous Restriction Factor" *Clin. Exp. Immunol.* 80:109–113.

Rooney et al., 1992. "Characterization of the Membrane Attack Complex Inhibitory Protein CD59 Antigen on Human Amniotic Cells and in Amniotic Fluid" *Immunol.* 76:541–547.

Waneck et al., 1988. "Conversion of a PI–Anchored Protein to an Integral Membrane Protein by a Single Amino Acid Mutation" *Science.* 24:697–699.

Rotoli et al., 1989, "Paroxysmal Nocturnal Hemoglobinuria" Seminars in Hematology, vol. 26, pp. 201–207.

```
CD59     MGI QGG SVL FGL LLV LAV FCH SGH S LQ CYN CPN PTA --- DCK
AGMCIP   MGI QGG SVL FGL LLA LAV FCH SGH S LQ CYN CPN PTT --- NCK
BABCIP   MGI QGG SVL FGL LLV LAV FCH SGH S LQ CYN CPN PTT --- DCK
OWMCIP   MGI QGG SVL FGL LLV LAV FCH SGN S LQ CYN CPN PTT --- QCT
MARCIP   MGI QGG SVL FGL LLI LAV FCH SGH S LQ CYS CPY PTT --- QCT
SQMCIP   MGI QGG SVL FGL LLV LAV FCH SGH S LQ CYS CPY STA --- RCT
                                                    CYS CPL PTM ESM ECT
HVS-15       M YIL FTL VLT F-V FCK PIH S LQ CYN CSH STM --- QCT

CD59     TAV NCS SDF DAC LIT KAG LQV YNK CWK FEH CNF NDV TTR LRE NEL
AGMCIP   TAI NCS SGF DTC LIA RAG LQV YNQ CWK FAN CNF NDI STL LKE SEL
BABCIP   TAI NCS SGF DTC LIA RAG LQV YNQ CWK FAN CNF NDI STL LKE SEL
OWMCIP   MTT NCT SNL DSC LIA KAG SRV YYR CWK FED CTF SRV SNQ LSE NEL
MARCIP   TTT NCT SNL DSC LIA KAG LRV YYR CWK FED CTF RQL SNQ LSE NEL
SQMCIP   AST NCT SNL DSC LIA KAG SGV YYR CWK FDD CSF KRI SNQ LSE TQL
         TST SCT SNL DSC LIA KAG SGV YYR CWK FDD CSF KRI SNQ LSE TQL
HVS-15

CD59     TYY CCK KDL CNF NEQ LEN GGT SLS EKT VLL LVT PFL AAA WSL HP
AGMCIP   QYF CCK EDL CN- -EQ LEN GGT SLS EKT VLL LVT PLL AAA WCL HP
BABCIP   QYF CCK KDL CNF NEQ LEN GGT SLS EKT VVL LVT LLL AAA WCL HP
OWMCIP   KYY CCK KNL CNF NEA LKN GGT TLS KKT VLL LVI PFL VAA WSL HP
MARCIP   KYH CCR ENL CNF NGI LEN GGT TLS KKT VLL LVT PFL AAA WSL HP
SQMCIP   KYH CCK KNL CNV LEN LEN GGT TLS KKT ILL LVT PFL AAA WSR HP
HVS-15   KYH CCK KNL CNV NKG IEN IKR TIS DKA LLL LLA LFL VTA WNF PL
```

FIG. 1

TERMINAL COMPLEMENT INHIBITOR FUSION PROTEINS

This is a divisional of U.S. Ser. No. 08/205,720, filed Mar. 3, 1994 (now abandoned).

FIELD OF THE INVENTION

The present invention relates to terminal complement inhibitory proteins that have been genetically engineered to alter their attachment to the cell surface and to medical uses of such novel molecules.

BACKGROUND OF THE INVENTION

I. The Complement System

The complement system acts in conjunction with other immunological systems of the body to defend against intrusion of cellular and viral pathogens. There are at least 25 complement proteins, which are found as a complex collection of plasma proteins and membrane cofactors. The plasma proteins make up about 10% of the globulins in vertebrate serum. Complement components achieve their immune defensive functions by interacting in a series of intricate but precise enzymatic cleavage and membrane binding events. The resulting complement cascade leads to the production of products with opsonic, immunoregulatory, and lytic functions.

The lytic aspect of complement function is effected by the permeablization of target cell membranes as a direct action of an assemblage of complement proteins known individually as "terminal complement components" and, in their functional assemblage, as the membrane attack complex, or "MAC". (See Esser, 1991; and Bhakdi, et al., 1991.) The actions of the MAC, hereinafter referred to as "complement attack," create pores or leaky patches that lead to the disruption of osmotic and ionic gradients in target cells, which, at high enough MAC concentrations, causes cell death. Lower concentrations of MACs can produce other effects, including activation of endothelial cells and platelets. Inappropriate MAC activity can result in pathologic damage to cells and tissues.

The complement cascade progresses via the classical pathway or the alternative pathway. These pathways share many components, and, while they differ in their early steps, both converge and share the same terminal complement components responsible for complement attack and the activation and/or destruction of target cells.

The classical complement pathway is typically initiated by antibody recognition of and binding to an antigenic site on a target cell. The alternative pathway is usually antibody independent, and can be initiated by certain molecules on pathogen surfaces. Both pathways converge at the point where complement component C3 is cleaved by an active protease (which is different in each pathway) to yield C3a and C3b. Other pathways activating complement attack can act later in the sequence of events leading to various aspects of complement function, including the formation of the MAC.

C3a is an anaphylatoxin that can induce degranulation of mast cells, resulting in the release of histamine and other mediators of inflammation. C3b has multiple functions. As opsonin, it binds to bacteria, viruses and other cells and particles and tags them for removal from the circulation. C3b can also form a complex with other components unique to each pathway to form classical or alternative C5 convertase, which cleaves C5 into C5a (another anaphylatoxin), and C5b, which is the first of the terminal complement components that make up the MAC. (Amongst the several means by which complement attack can be initiated, proteolytic enzymes with relatively broad target protein specificities, including plasmin, elastase, and cathepsin G, can cleave C5 so as to mimic the action of C5 convertase and produce active C5b.) C5b combines sequentially with C6, C7, and C8 to form the C5b-8 complex at the surface of the target cell. Upon binding of several C9 molecules, the active MAC (C5b-9) is formed.

II. Regulation of the Complement System

Normally, the complement system is in a continuous state of spontaneous turnover. C3 can spontaneously acquire C3b functions, forming a functional C3 convertase and leading to the formation of more C3b. The C3b generated in this spontaneous fashion can also form C5 convertase and thus initiate the final steps in the cascade that forms the MAC.

Under normal conditions, blood flow will dilute and disperse the low levels of spontaneously activated complement components thus helping to prevent MAC buildup in any one location in the vasculature. In addition, homeostatic regulation of the actions of autologous complement proteins to prevent autoimmune attack is mediated by specific endogenous complement inhibitor proteins (CIPs), that can be found on the surfaces of most human cells. Ordinarily, blood flow and the action of CIPs suffice to render cells resistant to normal levels of spontaneous complement activation without injury or lysis. Under conditions of acute inflammation, and in various disease states where complement activation and MAC formation are accelerated, the normal quantity and activity of endogenous complement inhibitors may be inadequate to protect autologous cells from MAC-induced lysis and/or sublytic MAC-induced cell activation. Endogenous CIP activity may also be insufficient where there is stasis of the blood, and/or where there are defects in or deficiencies of naturally occurring inhibitors.

A number of CIPs have been identified that serve to protect cells from damage mediated by complement from concordant species. See Zalman, et al., 1986; Schonermark, et al., 1986; Nose, et al., 1990; and Sugita, et al., 1988. These inhibitors act at various defined points in the complement cascade. For example, CD55, also known as decay accelerating factor (DAF), exerts its major inhibitory effects on the actions of C3 convertase.

In cases where the complement cascade is initiated at points in the pathway after the C3 convertase step, such as through the generation of active C5b by broad spectrum proteases, DAF and other complement inhibitors acting at earlier steps in the cascade sequence are ineffective. There are, however, inhibitors that do not share this deficiency. These inhibitors act at the final steps in MAC assembly and thus can effectively block complement attack initiated by almost any means. These inhibitors are known as "terminal complement inhibitors" or "terminal CIPs."

III. Terminal CIPs

The most thoroughly characterized terminal CIP is the human protein CD59 (also known as "protecting", "MACIF", or "p18"). CD59 is a glycoprotein with an apparent molecular mass of 18–21 kilodaltons that protects cells from complement-mediated lysis. CD59 is tethered to the outside of the cell by a glycosyl-phosphatidylinositol (GPI) glycolipid moiety that anchors it in the cell membrane. CD59 is found associated with the membranes forming the surfaces of most human cells including erythrocytes, lymphocytes, and vascular endothelial cells. (See, for example, Sims, et al., U.S. Pat. No. 5,135,916.)

CD59 appears to function by competing with C9 for binding to C8 in the C5b-8 complex, thereby decreasing the formation of the C5b-9 MAC (Rollins, et al., 1990). CD59 thus acts to reduce both cell stimulation and cell lysis by MACs (Rollins, et al., 1990; Rollins, et al., 1991; Stefanova, et al., 1989; Sugita, et al., 1988; Davies, et al., 1989; Holguin, et al., 1989; Okada, et al., 1989a; Meri, et al., 1990; Whitlow, et al., 1990; and Harada, et al., 1990). This activity of CD59 is for the most part species-selective, most efficiently blocking the formation of MACs under conditions where C8 and C9 are derived from homologous (i.e., human) serum (Venneker, et al., 1992).

The assimilation of purified CD59 into the plasma membrane of non-human erythrocytes (which are believed to be protected from homologous non-human complement attack by the action of their own cell surface complement inhibitor proteins) and oligodendrocytes (brain cells which are believed to be protected less, if at all, by cell surface proteins, but may be protected in vivo by the blood brain barrier) has shown that CD59 can protect these cells from cell lysis mediated by human complement. (Rollins, et al., 1990; Rollins, et al., 1991; Stefanova, et al., 1989; Meri, et al., 1990; Whitlow, et al., 1990; Okada, et al., 1989b; and Wing, et al., 1992).

cDNAs coding for CD59 have been cloned and the structure of the CD59 gene has been characterized (Davies, et al., 1989; Okada, et al., 1989b; Philbrick, et al., 1990; Sawada, et al., 1989; and Tone, et al., 1992). Non-human mammalian cells transfected with the cloned CD59 cDNA, and thereby expressing the human CD59 protein on their cell surfaces, have been shown to gain resistance to complement-mediated cell lysis (Zhao, et al., 1991; and Walsh, et al., 1991).

CD59 has been reported to be structurally related to the murine Ly-6 antigens (Philbrick, et al., 1990; and Petranka, et al., 1992). The genes encoding these antigens, also known as T-cell activating proteins, are members of the Ly-6 multigene family, and include Ly-6A.2, Ly-6B.2, Ly-6C.2, Ly6C.2, and Ly-6E.1. The gene encoding the murine thymocyte B cell antigen ThB is also a member of this family (Shevach, et al. 1989; and Gumley, et al., 1992).

A number of viral and non-human primate complement inhibitor proteins that are similar in structure and function to CD59 have been described (see Rother, et al., 1994; Albrecht, et al., 1992; commonly assigned, copending, U.S. patent application Ser. No. 08/105,735(now abandoned), filed Aug. 11, 1993, by William L. Fodor, Scott Rollins, Russell Rother, and Stephen P. Squinto, and entitled "Complement Inhibitor Proteins of Non-Human Primates;" and commonly assigned and copending PCT patent application Serial No. PCT/US93/00672, filed Jan. 12, 1993, by Bernhard Fleckenstein and Jens-Christian Albrecht, and entitled "Complement Regulatory Proteins of Herpesvirus Saimirill".

These proteins—BABCIP (SEQ ID NO:1), AGMCIP (SEQ ID NO:2), SQMCIP (SEQ ID NO:3), OWMCIP (SEQ ID NO:4), MARCIP (SEQ ID NO:5), and HVS-15 (SEQ ID NO:6)—all share striking sequence homologies, including a distinctive conserved arrangement of cysteines within their amino acid sequences. These conserved patterns are most readily perceived by aligning the sequences of the proteins so that the cysteine residues are in register as seen in FIG. 1.

Cysteine residues of many proteins form a structural element referred to in the art as a "cysteine backbone". In proteins in which they occur, cysteine backbones play essential roles in determining the three-dimensional folding, tertiary structure, and ultimate function of the molecule. The proteins of the Ly-6 multigene family, as well as several other proteins, share a particular cysteine backbone structure referred to herein as the "Ly-6 motif". For example, the human urokinase plasminogen activator receptor (uPAR; Roldan, et al., 1990) and one of several squid glycoproteins of unknown function (Sgp2; Williams, et al., 1988) contain the Ly-6 motif.

Subsets of proteins having the Ly-6 motif can be identified by the presence of conserved amino acid residues immediately adjacent to the cysteine residues. Such conservation of specific amino acids within a subset of proteins can be associated with specific aspects of the folding, tertiary structure, and ultimate function of the proteins. These conserved patterns are most readily perceived by aligning the sequences of the proteins so that the cysteine residues are in register.

As discussed fully in the above-referenced, copending U.S. patent application Ser. No. 08/105,735(now abandoned), the relevant portions of which are incorporated herein by reference, a series of non-human primate C5b-9 inhibitory proteins have been identified which are characterized by a cysteine backbone structure which defines a specific subset of the general Ly-6 motif.

Specifically, these non-human primate CIPs include polypeptides comprising a cysteine backbone with a Ly-6 motif characterized by the formula:

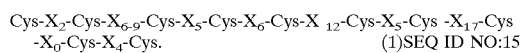
$$\text{Cys-X}_2\text{-Cys-X}_{6\text{-}9}\text{-Cys-X}_5\text{-Cys-X}_6\text{-Cys-X}_{12}\text{-Cys-X}_5\text{-Cys -X}_{17}\text{-Cys -X}_0\text{-Cys-X}_4\text{-Cys.} \quad (1)\text{SEQ ID NO:15}$$

In addition, the non-human primate C5b-9 inhibitory proteins include amino acid sequences conforming to the following formula:

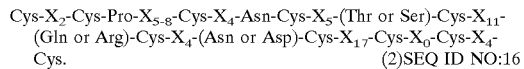
$$\text{Cys-X}_2\text{-Cys-Pro-X}_{5\text{-}8}\text{-Cys-X}_4\text{-Asn-Cys-X}_5\text{-(Thr or Ser)-Cys-X}_{11}\text{-} \text{(Gln or Arg)-Cys-X}_4\text{-(Asn or Asp)-Cys-X}_{17}\text{-Cys-X}_0\text{-Cys-X}_4\text{-Cys.} \quad (2)\text{SEQ ID NO:16}$$

In both formulas, the X in $X_n$ indicates a peptide containing any combination of amino acids, the n in $X_n$ represents the length in amino acid residues of the peptide, and each X at any position can be the same as or different from any other X of the same length in any other position.

As discussed fully in the above-referenced, copending, commonly assigned, PCT application Ser. No. PCT/US 93/00672, the relevant portions of which are incorporated herein by reference, and in Albrecht, et al., 1992, a protein of the herpesvirus saimiri having C5b-9 inhibitory activity has been discovered (referred to herein as "HVS-15"). This viral protein has the Ly-6 motif which is characteristic of the non-human primate C5b-9 inhibitory proteins discussed above, i.e., its structure is described by formulas (1) and (2) above.

In the discussion which follows, terminal CIPs comprising Ly-6 motifs are referred to as "Ly-6 terminal CIPs." These CIPs will in general satisfy formula (1) above and preferably also formula (2). Some variations, however, in the spacing between any two of the ten cysteines making up the Ly-6 motif and in the adjacent amino acids are to be expected in as yet uncharacterized terminal CIPs of other species.

Also, Petranka et al., 1993, and Norris, et al., 1993, have reported that in CD59 (SEQ ID NO:7) the disulfide bond between Cys6 and Cys13, as well as the disulfide bond between Cys64 and Cys69, can be disrupted by replacement of these cysteines with serines without substantially compromising the functionality of CD59. These cysteines correspond to the second, third, ninth, and tenth cysteines in the above formulas. Accordingly, as used herein, the term "Ly-6 terminal CIP" is intended to also include terminal complement inhibitor proteins conforming with the above formulas but with all or some of the second, third, ninth or tenth cysteines replaced with serine, or another amino acid.

IV. Other Cell Surface Complement Inhibitor Proteins

In addition to the Ly-6 terminal CIPs discussed above, other membrane bound CIPs have been described in the literature, including the following:

(a) CD46 (membrane cofactor protein, MCP, see, for example, PCT patent publication No. WO 91/02002) is a 350 amino acid transmembrane (TM) protein found on all cells except red blood cells. CD46 binds to C3b, and, once bound, promotes the activity of proteases that cleave C3b into inactive fragments, thus preventing C3b accumulation on the cell surface and, in turn, protecting cells from complement attack. Both membrane bound and secreted forms of CD46 have been reported in the literature (Purcell et al., 1991).

(b) CD55 (decay accelerating factor, DAF), mentioned above, is a GPI-anchored cell surface protein present on all cells including red blood cells. Unlike CD46, CD55 does not destroy C3b. Rather, CD55 prevents C3b from reacting with other complement components, thus contravening complement mediated cytolysis. Both membrane bound and secreted forms of CD55 have been reported in the literature (Moran et al., 1992).

(c) CD35 (complement receptor 1, CR1) is found on a select group of lymphocytes as well as erythrocytes, neutrophils, and eosinophils, and causes degradation of C3b molecules adhering to neighboring cells.

(d) Factor H and C4b-binding protein, both of which inhibit alternative C3 convertase activity.

V. Transplantation

Intrinsic activation of complement attack via the alternative pathway during storage of donor organs is responsible for certain problems associated with organ transplantation which arise as a result of endothelial cell stimulation and/or lysis by the C5b-9 MAC (Brasile, et al. 1985). Ex vivo complement attack leads to reduced vascular viability and reduced vascular integrity when stored organs are transplanted, increasing the likelihood of transplant rejection.

Ten percent of allogeneic transplanted kidneys with HLA-identical matches are rejected by in vivo immunologic mechanisms (Brasile, et al. 1987). In 78% of the patients who reject organs under these conditions, cytotoxic antibodies binding to molecules on the surfaces of vascular endothelial cells are seen (Brasile, et al., 1987). Such antibody cytotoxicity is mediated by complement attack, and is responsible for the rejection of transplanted solid organs including kidneys and hearts (Brasile, et al., 1987; Brasile et al., 1985). Antibody primed, complement-mediated rejection is usually rapid and irreversible, a phenomenon referred to as hyperacute rejection.

In the xenogeneic setting, as when non-human organs are transplanted into human patients, activation of complement attack by antibodies directed against molecules on the surfaces of endothelial cells lining the vessels of the donor organ is almost always observed. The prevalence of such xenoreactive antibodies accounts for the nearly universal occurrence of hyperacute rejection of xenografts (Dalmasso, et al., 1992). Old world primates, including humans, have high levels of preexisting circulating "natural" antibodies that predominantly recognize carbohydrate determinants expressed on the surface of xenogeneic cells from discordant species. Recent evidence indicates that most of these antibodies react with galactose in an α1-3 linkage with galactose (Gal (α1-3)Gal) (Sandrin, et al., 1993).

Old world primates lack the appropriate functional α-1, 3-galactose transferase and thus do not express this carbohydrate epitope. Therefore, following transplantation of a vascularized xenogeneic donor organ, these high-titer antibodies bind to the Gal(α1-3)Gal epitope on the vascular endothelium and activate the recipient's complement through the classical pathway. The massive inflammatory response that ensues from activation of the complement cascade leads to the destruction of the donor organ within minutes to hours.

Xenoreactive antibodies are not exclusively responsible for hyperacute rejection of discordant organs in all cases. For example, erythrocytes from some species can activate human complement via the alternative pathway and newborn piglets raised to be free of preformed antibodies reject xenografts almost immediately. It is therefore likely that in some species combinations, activation of the alternative complement pathway contributes to graft rejection.

Endogenously-expressed, membrane-associated complement inhibitory proteins normally protect endothelial cells from autologous complement. However, the species restriction of complement inhibitors makes them relatively ineffective with respect to regulating discordant xenogeneic serum complement. The lack of effective therapies aimed at eliminating this antibody and complement-mediated hyperacute rejection presents a major barrier to the successful transplantation of discordant animal organs into human recipients.

Recently, a report on a baboon-to-human liver transplant has been published in which the xenogeneic donor organ failed to exhibit signs of hyperacute rejection (Starzl, et al., 1993). The low levels of anti-baboon antibodies likely to be present in human blood make hyperacute responses less likely. However, it is believed that recently discovered baboon CIPs, which have been shown to be related to CD59 and to be effective against human complement, also played a role in maintaining the integrity of this xenotransplanted organ. (See U.S. patent application Ser. No. 08/105,735(now abandoned), referred to above.)

The lack of hyperacute rejection seen in the baboon to human xenotransplant discussed above suggests that complement inhibitor proteins effective against human complement may, in combination with other anti-rejection strategies, allow safe and effective xenotransplantation of transgenic animal organs expressing such proteins into human patients.

VI. GPI-Anchored CIPs and Modifications Thereof

GPI-anchored terminal CIPs share certain properties that make them less desirable than transmembrane (TM) proteins for use as complement inhibiting agents for the protection of transplanted cells or organs.

GPI-anchored terminal CIPs, including CD59, BABCIP, and AGMCIP, can be cleaved from cell surfaces by specific phospholipase enzymes that hydrolyze GPI anchors. Such phospholipases are present in the serum (phospholipase D, Davitz, et al., 1987), and may also be released from cells in response to ischemia (phospholipase C, Vakeva, et al., 1992). Since ischemia is an unavoidable concomitant of transplantation, the process of transplantation may serve to remove native and/or artificially introduced GPI-anchored terminal CIPs from the very cells within the transplanted organ that they are meant to protect.

Another mechanism by which GPI-anchored proteins are removed from the cell surface is the incorporation of such proteins into membrane vesicles and the subsequent shedding of the vesicles from the cell. Such vesiculation can occur in response to various stimuli, such as ischemia-induced complement attack. It has been reported that GPI-anchored proteins are concentrated in these vesicles relative to their concentration in the cell membrane, a phenomenon that may reflect involvement of these proteins in the vesiculation process itself (Butikofer, et al., 1989; Brown, et al., 1992; Whitlow, et al., 1993). Such preferential incorporation into shed vesicles can reduce the concentrations of GPI-anchored proteins on the cell surface, including the concentrations GPI-anchored terminal CIPs. Such reductions of terminal CIP concentrations, particularly in response to complement attack, may occur at just those times when inhibition of complement is most needed.

In addition to their susceptibility to removal from the cell surface, GPI-anchored proteins also suffer from the problem that their production may be limited in various cell types. That is, only so many GPI-anchored molecules can normally be produced by a cell within a given time frame, so that introducing genes for further GPI-anchored proteins may not in fact result in substantial increases in the amount of protein actually present on the cell surface.

The limiting case of this problem involves cells which are incapable of producing any GPI-anchored proteins. The clinical disease of paroxysmal nocturnal hemoglobinuria (PNH) involves cells of this type, specifically, blood cells which do not produce GPI-anchored terminal CIPs. As discussed in copending, commonly assigned, U.S. patent application Ser. No. 08/206,189 (now abandoned), entitled "Method for the Treatment of Paroxysmal Nocturnal HemoglobinuriaII", which is being filed concurrently herewith in the names of Russell Rother, Scott A. Rollins, Seth A. Fidel, and Stephen P. Squinto, PNH cells can be made resistant to complement attack through the use of the transmembrane terminal CIPs described herein.

A further drawback of GPI-anchored proteins involves the ability of these proteins to transduce signals into the cell upon being cross-linked by specific antibodies and presumably upon binding their natural ligand (Okada, et al., 1989b; Seaman, et al., 1991; Su, et al., 1991; Deckert, et al., 1992; Cinek, et al., 1992; Card, et al., 1991; Groux, et al., 1989; and Stefanova, et al., 1991). Possible undesirable cellular responses to such intracellular signals can include phospholipase activation and/or release, and the stimulation of vesicle formation and shedding, both of which, as discussed above, can result in the loss of GPI-anchored proteins from the cell surface. Thus, the very GPI-anchored terminal CIPs that are used to protect the cells of a transplanted organ from complement attack may activate the cellular events that lead to their removal from the cell surface.

Work has been performed in which the means of attachment of GPI-anchored proteins to the outer cell surface has been varied from their natural GPI anchors by substitution of other anchoring moieties (Su, et al., 1991; and Lublin, et al., 1991).

For example, chimeric derivatives of CD55, containing amino acids 1–304 of CD55 fused to a fragment of CD46 which includes the protein's transmembrane domain (i.e., amino acids 270–350 of CD46) or to a fragment of the human major histocompatibility protein HLA-B44 which includes its transmembrane domain (i.e., amino acids 262–338 of HLA-B44), have been reported to retain levels of function equivalent to native CD55 (Lublin, et al., 1991). Significantly, with regard to the present invention, no such substitutions have been made with terminal CIPs and no such molecules have been developed for clinical use and, in particular, for use in constructing transgenic organs for transplantation.

VII. Protein Structure and Function

Minor alterations of protein primary structures (amino acid sequences) can have profound effects on their functional properties. The best known example of this phenomenon is in the case of sickle cell anemia, in which a single amino acid alteration, namely, a change in residue 6 of the beta chain of hemoglobin from Glu to Val, is sufficient to change the oxygen binding properties of the hemoglobin molecule and to thereby cause sickle cell disease.

The insertion of heterologous amino acid sequences representing new domain structures into a protein can also have significant effects on the protein's functional properties. For example, the introduction of a 10 amino acid epitope of the c-myc proto-oncogene (known as the myc tag) to the int-1proto-oncogene alters the functional properties of int-1. Specifically, C57MG mammary epithelial cells are transformed by wild-type int-1, but not by the mvc-tagged int-1, while residual function of the mvc-tagged int-1 gene is seen in a more sensitive assay examining effects on Drosophila development (McMahon et al., 1989).

Additionally, substitution of homologous sequences from heterologous proteins can have profound effects on protein function. For example, replacement of either of the two most carboxyl-terminal 12 amino acid segments of the mouse nerve growth factor gene with homologous segments from the related mouse brain derived neurotrophic factor gene reduces the activity of the molecule by 50%. That is, the carboxyl-terminal region is particularly sensitive to substitution with a homologous sequence from a heterologous protein, such a substitution having sufficient impact on protein function to decrease activity by 50%. A similar decrease in activity is seen following substitution of the amino terminus (Suter, et al., 1992).

All Ly-6 terminal CIPs are believed to share the property of being attached to cell membranes by means of a GPI linkage. As understood in the art, the addition of such a GPI moiety to a nascent protein coincides with a proteolytic processing step that removes a number of amino acid residues from the carboxyl-terminus of the polypeptide. Accordingly, mature Ly-6 terminal CIPs do not include all of the amino acids specified by the full length nucleic acid molecules that encode them. Specifically, they do not include some or all of the amino acid residues downstream of the cysteine backbone Ly-6 motif, e.g., the amino acids downstream of cysteine 69 of SEQ ID NO:1, SEQ ID NO:2, SEQ ID NO:4, SEQ ID NO:5, SEQ ID NO:6, SEQ ID NO:7 (CD59) and downstream of cysteine 72 of SEQ ID NO:3. (As used herein, "downstream" means towards the carboxyl terminus of the polypeptide or towards the 3' end of the coding strand of the nucleic acid molecule coding for the polypeptide and "upstream" means towards the amino terminus of the polypeptide or towards the 5' end of the coding strand of the nucleic acid molecule coding for the polypeptide.) It is not known which amino acids downstream of the Ly-6 cysteine backbone motif are present or absent in any of these terminal CIPs when they are in the mature, GPI anchored state.

As discussed in detail below, the present invention involves the removal of selected amino acids of such Ly-6 terminal CIPs downstream of the Ly-6 motif. In view of the foregoing state of the art, it was not known, prior to the present invention, what effects such amino acid removal would have on terminal CIP function. In particular, it was not known if Ly-6 terminal CIPs would retain any complement inhibitory activity after such removal.

Various attempts have been made to examine the effects of GPI anchors on protein function. In the case of CD55, the substitution of protein fragments that contain a transmembrane domain for the carboxyl-terminal sequences believed to be involved in the addition of the GPI anchor (referred to hereinafter as the "GPI signal sequence") results in a protein with equal activity to the native GPI-anchored protein (Lublin, et al., 1991). In the case of the Ly-6 protein, Ly-6E (Ly-6E.1), which is a GPI-anchored cell surface protein that is structurally related to CD59 (Philbrick, et al. 1990), the substitution of a fragment containing a transmembrane domain for the carboxyl-terminal GPI signal sequences downstream of the Ly-G motif produces a non-functional protein, i.e., a protein-which is not capable of activating T-cells (Su, et al., 1991).

SUMMARY OF THE INVENTION

In view of the foregoing, it is an object of this invention to provide novel proteins that can be used in controlling the complement system of humans and other animals. It is a further object of the invention to provide nucleic acid sequences and associated genetic engineering constructs for producing such proteins either in vitro or in vivo.

More particularly, it is the object of the invention to provide novel proteins that are Ly-6 terminal complement inhibitors, but are anchored to the cell surface by means independent of GPI anchoring. It is an additional object of the invention to provide molecules of this type that will not transmit an activating signal into the cells to which they are bound, e.g., endothelial cells, lymphocytes, or platelets, either after antibody crosslinking, or upon binding of the terminal CIP to its ligand. It is a further object of the invention to provide molecules of this type that cannot be removed from the surfaces of the cells to which they are bound by the actions of lipid cleaving enzymes such as phospholipases and which are not preferentially incorporated into shed vesicles.

To achieve the foregoing and other objects, the present invention, in accordance with certain of its aspects, provides the complete cDNA sequences of chimeric genes encoding chimeric protein products which comprise the fusion of a Ly-6 terminal CIP with a heterologous transmembrane (TM) domain. Prior to fusion, selected amino acid residues located downstream from the Ly-6 motif of the terminal CIP are deleted. The invention also comprises the chimeric protein products encoded by these genes, such chimeric molecules being referred to hereinafter as TMTCIPs (i.e., transmembrane terminal complement inhibitor proteins). In the preferred embodiments of the invention, the chimeric proteins have greater than 50% of the complement inhibitory activity of the native, GPI-anchored terminal CIP from which the TMTCIP is derived where such activity is preferably measured using a dye release assay of the type described below in Example 4.

The protection from complement attack offered by the TMTCIPs of the invention can be provided via gene transfer for the therapeutic prevention of pathologic complement attack in, for example, transplantation. In a preferred form of such therapy, the expression of the TMTCIP can be directed to the surfaces of cells of non-human animal organs, e.g., organs of non-human transgenic animals, in order to protect such organs from complement attack upon transplantation into a human patient.

The accompanying drawings, which are incorporated in and constitute part of the specification, illustrate certain aspects of the preferred embodiments of the invention and, together with the description, serve to explain certain principles of the invention. It is to be understood, of course, that both the drawings and the description are explanatory only and are not restrictive of the invention.

BRIEF DESCRIPTION OF THE DRAWINGS

FIG. 1 shows aligned amino acid sequences of Human, African Green Monkey, Baboon, Owl Monkey, Marmoset, Squirrel Monkey, and Herpesvirus Saimiri Ly-6 terminal CIPs (CD59, AGMCIP, BABCIP, OWMCIP, MARCIP, SQMCIP, and HVS-15, respectively). The cysteine residues making up the Ly-6 cysteine backbone motif of each protein are underlined.

FIG. 4A shows data obtained using a clone expressing the native human CD59 molecule (CD59-GPI). FIG. 4B shows data obtained using a clone expressing the CD59-MCP TMTCIP (CD59-TM). In each panel, the traces labeled "A" and "B" represent cells stained with the secondary antibody alone, without or with PI-PLC treatment, respectively. In each panel, the traces labeled "C" and "D" represent cells stained with both the primary (CD59 specific) antibody and the secondary antibody with or without PI-PLC treatment, respectively.

DESCRIPTION OF THE PREFERRED EMBODIMENTS

Figure 2:
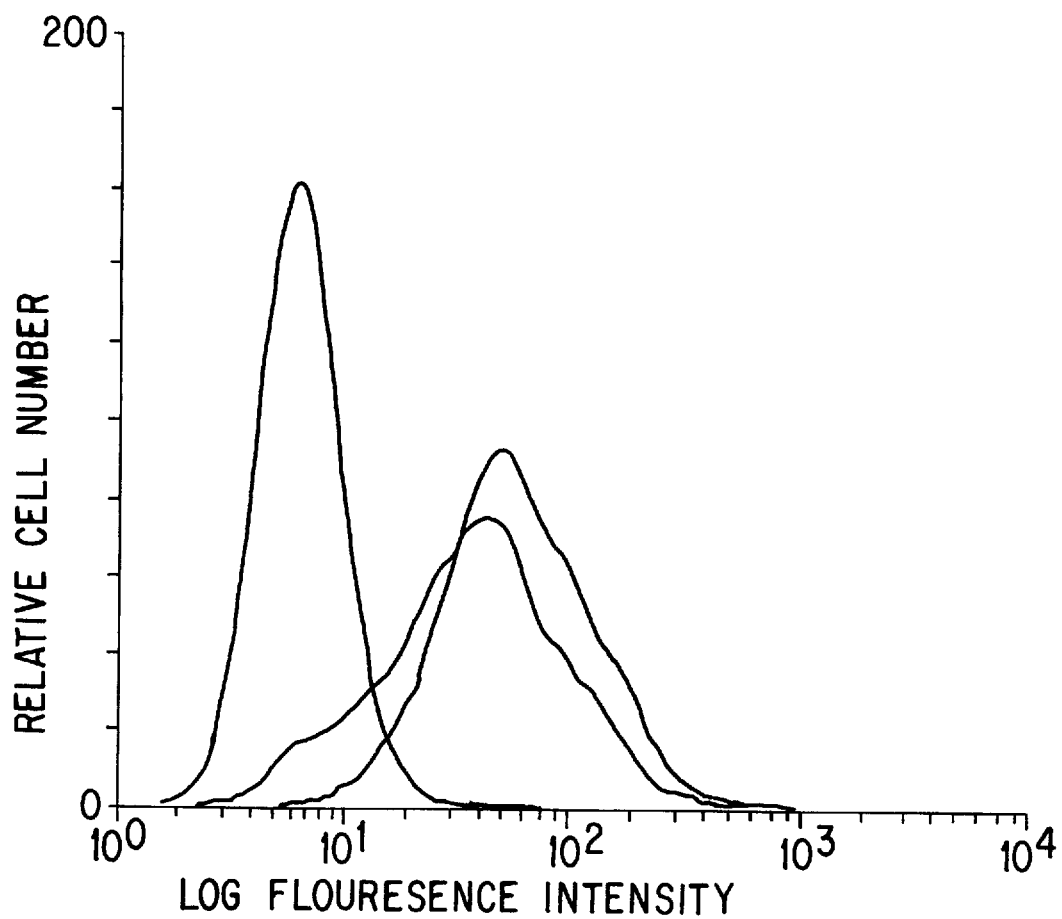
FIG. 2 shows a comparison of the cell surface expression of CD59 epitopes on Balb/3T3 cells. The three traces represent cell surface expression profiles of a positive Balb/3T3 clone expressing the CD59-MCP TMTCIP (CD59-TM), a native human CD59 transfectant (CD59-GPI) as a positive control and a vector (pcDNA3, Invitrogen, San Diego, Calif.) without insert transfectant (Vector Control) as a negative control.

As discussed above, the present invention provides the complete CDNA sequences of chimeric genes encoding chimeric protein products which comprise the fusion of a Ly-6 terminal CIP and a heterologous transmembrane domain.

I. Terminal CIPs

A variety of terminal CIPs can be used in the practice of the invention. In particular, Ly-6 terminal CIPs can be used. In addition to sharing the homologies shown in formulas (1) and (2) above, the Ly-6 terminal CIPs also share a variety of other homologies which can be seen in the aligned amino acid sequences of FIG. 1. Homologies found downstream from the Ly-6 cysteine motif of these terminal CIPs include an N immediately following the last C of the Ly-6 motif, another N 6–8 residues downstream from the last C of the Ly-6 motif (referred to herein as the "truncation-Asn"), and the following consensus sequence, hereinafter referred to as the "downstream consensus sequence" which includes the aforementioned truncation-Asn at the third position in the sequence:

(L or I) (E or K) N (G or I) (G or K) (T or R) (S or T) (L or I) S (K or E or D) K (T or A) (V or I or L) (L or V) L L (V or L)

(A or T or I) (P or L) (F or L) L (A or V) (A or T) A W (S or C or N) (L or R or F) (H or P) (P or L) (SEQ ID NO: 17).

In addition to these structural commonalities, testing of the Ly-6 terminal CIPs of FIG. 1 has shown that they share the ability to substantially inhibit the activity of human complement. (See U.S. patent application Ser. No. 08/105,735 (now abandoned), and PCT patent application Ser. No. PCT/US93/00672, referred to above.) In particular, each of CD59, AGMCIP, BABCIP, OWMCIP, SQMCIP, and HVS-15 had substantial human complement inhibitory activity. MARCIP was not tested, but is also expected to have such activity.

II. Transmembrane Domains

As known in the art, transmembrane proteins may span the membrane once or several times along the length of their amino acid chains. There are in general two different ways in which a transmembrane protein that spans the membrane only once may be embedded in a membrane. Most commonly, these proteins have their single transmembrane domain located towards the carboxyl-terminal end of the polypeptide chain and are oriented so that the region amino-terminal to the transmembrane domain is outside the cell or in a non-cytoplasmic cellular compartment and the region carboxyl-terminal to the transmembrane domain is in the cytoplasmic compartment. The second orientation of a transmembrane protein with a single membrane spanning transmembrane domain is the opposite of this common arrangement, that is, the region amino-terminal to the transmembrane domain is in the cytoplasmic compartment and the region carboxyl-terminal to the transmembrane domain is located outside the cell or in a non-cytoplasmic cellular compartment.

Other transmembrane proteins cross the membrane several-times. Most commonly, eukaryotic representatives of this type of transmembrane protein have seven consecutive transmembrane domains, most of them connected by short hydrophilic loop regions.

Transmembrane proteins in general include at least one contiguous stretch of amino acid residues which resides in the lipid bilayer membrane (referred to hereinafter as "membrane amino acids"), and at least two contiguous stretches of amino acid residues which extend away from the membrane, one generally cytoplasmic (referred to hereinafter as "cytoplasmic amino acids"), and one generally extracellular or sequestered in a non-cytoplasmic cellular compartment (referred to hereinafter as "extracellular amino acids"). As referred to herein, cytoplasmic amino acids and extracellular amino acids always include at least one charged amino acid residue immediately adjacent to the membrane amino acids (referred to herein as the "first cytoplasmic amino acid" and the "first extracellular amino acid," respectively).

Membrane amino acids are characterized as groups of at least about 20 amino acids (the minimum generally needed to span a membrane), most of which are hydrophobic (uncharged) amino acids. Charged (hydrophilic) amino acids are usually absent from these groups, but in some cases two hydrophilic residues of opposite charge may lie close together inside the membrane where they neutralize each other.

Transmembrane domains derived from a variety of transmembrane proteins can be used in the practice of the invention. However, transmembrane domains with cytoplasmic amino acids which include cysteine residues in close proximity to the first cytoplasmic amino acid may be expressed at lower levels on the cell surface than transmembrane domains that do not contain such cysteines. This decreased expression is believed to result from the propensity of these cysteine residues to form intermolecular bonds with similarly placed cysteines of adjacent nascent transmembrane protein molecules. Such intermolecular cysteine linkages cause aggregation of the nascent transmembrane proteins, generally within the Golgi apparatus (where newly synthesized transmembrane proteins are processed within the typical cell), and thus block the transport of such nascent proteins to the cell surface.

With regard to the TMTCIP molecules of the invention, it is notable that transfection of mammalian cells with an expression vector encoding a chimeric terminal CIP containing a putative transmembrane domain from the herpesvirus saimiri CCPH gene (see PCT patent application Ser. No. PCT/US93/00672, mentioned above) does not result in high enough levels of cell surface expression of terminal CIP epitopes to be detected by FACS analysis (see Example 1). The cytoplasmic amino acids of this putative transmembrane domain include cysteine residues spaced two and five amino acids from the first cytoplasmic amino acid, a histidine. The presence of these cysteines is believed to be responsible for the low levels of expression seen with this putative transmembrane domain. For this reason, transmembrane domains of this type are not preferred for use with the present invention.

As used herein, the term "transmembrane domain" is intended to comprise: 1) the portion of a transmembrane protein which spans the membrane, i.e., the at least about twenty membrane amino acids normally required for this purpose, 2) the adjacent predominantly charged cytoplasmic amino acids within about five to about ten residues from the membrane amino acids, and 3) the adjacent predominantly charged extracellular amino acids within about five to about ten residues from the membrane amino acids. These adjacent predominantly charged cytoplasmic and extracellular amino acids are involved in anchoring the protein in the membrane. As discussed above, preferred transmembrane domains do not include cytoplasmic amino acids that are cysteine residues within five amino acids of the first cytoplasmic amino acid.

While it is possible to examine a protein sequence and pick out a region with about 20 consecutive hydrophobic amino acids, some transmembrane domains, as discussed above, contain a small number of hydrophilic amino acids interspersed within their predominantly hydrophobic residues. Accordingly, transmembrane domains are more effectively identified by using hydrophobicity scales to compute hydropathy plots (Branden, et al., 1991).

Hydrophobicity scales provide a numerical value for the hydrophobicity of individual amino acids. These scales have been developed on the basis of solubility measurements of amino acids in different solvents, vapor pressures of side-chain analogues, analysis of side-chain distributions within soluble proteins, and theoretical energy calculations (Kyte, et al., 1982; and Engelman, et al., 1986).

Hydropathy plots are computed from amino acid sequences using hydrophobicity values as follows. First, for each position in the sequence, a hydropathic index is calculated. The hydropathic index is the mean value of the hydrophobicity of the amino acids within a "window," usually 19 residues long, around each position. The hydropathic indices are then plotted versus amino acid sequence position to produce the hydropathy plot.

Transmembrane domains are then identified from the hydropathy plots by searching for regions where the hydropathic index is high for a number of consecutive positions in the sequence, e.g., by searching for regions with broad peaks with high positive (i.e., hydrophobic) values.

In terms of the present invention, the transmembrane domain will preferably have a hydropathic index greater than about +0.5, using the scale of Kyte et al. (Kyte et al., 1982) and a window of 19 amino acids, over a region of at least about 12 amino acid residues.

Additional contiguous amino acids of the transmembrane protein can be included in or encoded by the chimeric molecules of the invention provided those additional amino acids do not substantially impair the insertion of the transmembrane domain into the membrane, the transport of the nascent chimeric protein to the cell surface, or the complement inhibitory activity of the terminal CIP portion of the chimeric molecule.

While the molecules of the present invention may be constructed with any functional transmembrane domain, one derived from a protein with only a single transmembrane domain and having the region carboxyl-terminal to its transmembrane domain in the cytoplasm is preferred. A large number of such proteins have been reported in the literature, including the following: CD46; the major histocompatibility antigens and related transmembrane proteins of the immunoglobulin multigene superfamily including intercellular adhesion molecules, such as ICAM-1 (CD54), ICAM-2, ICAM-3, VCAM-1, PECAM-1 (CD31) and HCAM (CD44); the selecting, including E-selectin, L-selectin, and P-selectin (CD62); the Alzheimer's amyloid precursor protein; the insulin receptor; the epidermal growth factor receptor; the gp41protein of the AIDs virus, HIV; the p21 proteins of HTLV1 and HTLV2; and the p15E proteins of the murine and feline leukemia viruses.

TM domains derived from any of these proteins, as well as from other transmembrane proteins, can be used in the practice of the invention. These domains can be most easily used by incorporating into the chimeric molecule the entire carboxyl end of the transmembrane protein beginning at a point upstream from the transmembrane domain. A particularly preferred TIM domain is that constituting amino acids 294 to 326 of CD46 (MCP, SEQ ID NO:8). This domain can be conveniently used along with amino acids 327 to 350, which comprise the carboxyl end of the CD46 protein downstream from the transmembrane domain of this molecule, and along with amino acids 270 to 293 upstream of the TM domain which do not interfere with insertion of the CD46 TM domain into cell membranes and, as shown below, do not inhibit the complement inhibitory activity of Ly-6 terminal CIPs.

In addition to using hydropathy plots to identify TM domains suitable for use in the present invention, such domains can also be identified biochemically using, for example, protease digestion techniques or by making chimeric molecules containing soluble proteins operatively linked to signal sequences and containing putative transmembrane domains, and assaying for membrane insertion of the chimeric protein.

III. TMTCIP Genes and Vectors Containing Such Genes

The isolation, truncation, and fusion of the nucleic acid fragments encoding the terminal CIP and the TM domain are performed using recombinant nucleic acid techniques known in the art, including: PCR generation of the desired fragments and/or restriction digestion of cloned genes; PCR fusion of the desired fragments; or enzymatic ligation of restriction digestion products (Sambrook, et al., 1989; and Ausubel et al., 1992). Alternatively, the nucleic acid molecules encoding the TMTCIPs of the invention or any or all of the nucleic acid fragments used to assemble the chimeric genes for the TMTCIPs can be synthesized by chemical means (Talib, et al., 1991).

The chimeric genes of the invention are prepared by 1) truncating the nucleic acid sequence for a Ly-6 terminal CIP so as to remove selected amino acid residues downstream of the Ly-6 motif in order to inactivate the normal GPI signal sequence, and 2) fusing the truncated sequence to a sequence coding for a selected TM domain and desired amino acids surrounding the TM domain.

The truncation of the nucleic acid sequence encoding the Ly-6 terminal CIP will remove at least some of the carboxyl-terminal amino acid residues downstream from the Asn which is located between 6 and 8 amino acid residues after the last (tenth) Cys of the Ly-6 motif. This Asn is also located at the third position in the downstream consensus sequence presented above, i.e., it is the truncation-Asn defined above. All known Ly-6 terminal CIPs include such a truncation-Asn.

In some cases, all of the amino acid residues after the truncation-Asn are removed. Alternatively, less than all can be removed, the criterion being that sufficient numbers of residues are removed so that the GPI signal sequence is inoperative. In general, the simplest approach is to remove all amino acid residues downstream of the truncation-Asn. If desired, the truncation can extend further upstream from the truncation-Asn, preferably starting at a point downstream from the last Cys of the Ly-6 motif. Truncations beginning upstream from the last Cys of the Ly-6 motif are in general not preferred, but can be used if desired. The criterion for truncations upstream of the truncation-Asn is the requirement that the TMTCIP has greater than 50%; of the complement inhibitory activity of the parent (native) Ly-6 terminal CIP.

In terms of the Ly-6 terminal CIPs of FIG. 1, the preferred truncation comprises all of the amino acids downstream of Asn 77 of BABCIP (SEQ ID NO:1), Asn 75 of AGMCIP (SEQ ID NO:2), Asn 80 of SQMCIP (SEQ ID NO:3), Asn 77 of OWMCIP (SEQ ID NO:4), Asn 77 of MARCIP (SEQ ID NO:5), Asn 77 of HVS-15 (SEQ ID NO:6), and Asn 77 of CD59 (SEQ ID NO:7). Of these Ly-6 terminal CIPs, CD59 is preferred. As discussed above, a preferred TM domain is from CD46. Accordingly, a particularly preferred embodiment of the invention comprises residues 1–77 of CD59 (SEQ ID NO:7) fused to amino acids 270–350 of CD46 (SEQ ID NO:8)

In addition to the foregoing, the present invention provides recombinant expression vectors which include nucleic acid fragments encoding the chimeric TMTCIPs of the invention. The nucleic acid molecule coding for such a chimeric protein can be inserted into an appropriate expression vector, i.e., a vector that contains the necessary elements for the transcription and translation of the inserted protein-encoding sequence. The necessary transcriptional and translational signals can also be supplied by the genes used to construct the fusion genes of the invention and/or their flanking regions.

The transcriptional and translational control sequences for expression vector systems to be used to direct expression in vertebrate cells may be provided by viral sources. For example, commonly used promoters and enhancers are derived from Polyoma virus, Adenovirus, Simian Virus 40 (SV40), the Molony murine leukemia virus (MMLV), including the long terminal repeat (MMLV-LTR), and human cytomegalovirus (CMV), including the cytomegalovirus immediate-early gene 1 promoter and enhancer. Retroviral expression vectors are a preferred system for expression of the TMTCIPs of the invention.

The manipulation of retroviral nucleic acids to construct retroviral vectors and packaging cells is accomplished using techniques known in the art. See Ausubel, et al., 1992, Volume 1, Section III (units 9.10.1–9.14.3); Sambrook, et al., 1989; Miller, et al., 1989; Eglitis, et al., 1988; U.S. Pat. Nos. 4,650,764, 4,861,719, 4,980,289, 5,122,767, and 5,124,263; as well as PCT Patent Publications Nos. WO 85/05629, WO 89/07150, WO 90/02797, WO 90/02806, WO 90/13641, WO 92/05266, WO 92/07943, WO 92/14829, and WO 93/14188.

In particular, the retroviral vectors of the invention can be prepared and used as follows. First, a TMTCIP retroviral vector is constructed and packaged into non-infectious transducing viral particles (virions) using an amphotropic packaging system, preferably one suitable for use in gene therapy applications.

Examples of such packaging systems are found in, for example, Miller, et al., 1986; Markowitz, et al., 1988; Cosset, et al., 1990; U.S. Pat. Nos. 4,650,764, 4,861,719, 4,980,289, 5,122,767, and 5,124,263, and PCT Patent Publications Nos. WO 85/05629, WO 89/07150, WO 90/02797, WO 90/02806, WO 90/13641, WO 92/05266, WO 92/07943, WO 92/14829, and WO 93/14188. A preferred packaging cell is the PA317 packaging cell line (ATCC CRL 9078).

The generation of "producer cells" is accomplished by introducing retroviral vectors into the packaging cells. Examples of such retroviral vectors are found in, for example, Korman, et al., 1987; Morgenstern, et al., 1990; U.S. Pat. Nos. 4,405,712, 4,980,289, and 5,112,767; and PCT Patent Publications Nos. WO 85/05629, WO 90/02797, and WO 92/07943. A preferred retroviral vector is the MMLV derived! expression vector pLXSN (Miller, et al., 1989). The retroviral vector used in the practice of the present invention will be modified to include the chimeric gene encoding the TMTCIP.

The producer cells generated by the foregoing procedures are used to produce the retroviral vector particles (virions). This is accomplished by culturing of the cells in a suitable growth medium. Preferably, the virions are harvested from the culture and administered to the target cells which are to be transduced, e.g., xenogeneic cells to be used for transplantation into a patient whose complement can be inhibited by the Ly-6 terminal CIP of the TMTCIP, cells of a xenogeneic organ to be used for transplantation into such a patient, the patient's own cells, and other cells to be protected from complement attack, as well as stem cells such as embryonic stem cells, which can be used to generate transgenic cells, tissues, or organs for transplantation. Alternatively, when practicable, the target cells can be co-cultured with the producer cells. Suitable buffers and conditions for stable storage and subsequent use of the virions can be found in, for example, Ausubel, et al., 1992.

Pharmaceutical compositions containing the retroviral vector particles of the invention can be administered in a variety of unit dosage forms. The dose will vary according to, e.g., the particular vector, the manner of administration, the particular disease being treated and its severity, the overall health and condition and age of the patient, the condition of the cells being treated, and the judgment of the physician. Dosage levels for transduction of mammalian cells are generally between about $10^6$ and $10^{14}$ colony forming units of retroviral vector particles per treatment.

A variety of pharmaceutical formulations can be used for administration of the retroviral vector particles of the invention. Suitable formulations are found in, for example, *Remington's Pharmaceutical Sciences*, Mack Publishing Company, Philadelphia, Pa., 17th ed., 1985, and will include a pharmaceutically effective carrier, such as saline, buffered (e.g., phosphate buffered) saline, Hank's solution, Ringer's solution, dextrose/saline, glucose solutions, and the like. The formulations may contain pharmaceutically acceptable auxiliary substances as required, such as, tonicity adjusting agents, wetting agents, bactericidal agents, preservatives, stabilizers, and the like.

IV. Transgenic Animals

In accordance with certain aspects of the invention, the nucleic acid molecules of the present invention are used to generate engineered transgenic animals (for example, rodent, e.g., mouse, rat, capybara, and the like, lagomorph, e.g., rabbit, hare, and the like, ungulate, e.g., pig, cow, goat, sheep, and the like, etc.) that express the TMTCIPs of the invention on the surfaces of their cells (e.g., endothelial cells) using techniques known in the art. These techniques include, but are not limited to, microinjection, e.g., of pronuclei, electroporation of ova or zygotes, nuclear transplantation, and/or the stable transfection or transduction of embryonic stem cells derived from the animal of choice.

A common element of these techniques involves the preparation of a transgene transcription unit. Such a unit comprises a DNA molecule which generally includes: 1) a promoter, 2) the nucleic acid sequence of interest, i.e., the sequence encoding the TMTCIP of the present invention, and 3) a polyadenylation signal sequence. Other sequences, such as, enhancer and intron sequences, can be included if desired. The unit can be conveniently prepared by isolating a restriction fragment of a plasmid vector which expresses the TMTCIP protein in, for example, mammalian cells. Preferably, the restriction fragment is free of sequences which direct replication in bacterial host cells since such sequences are known to have deleterious effects on embryo viability.

The most well known method for making transgenic animals is that used to produce transgenic mice by superovulation of a donor female, surgical removal of the egg, injection of the transgene transcription unit into the pronuclei of the embryo, and introduction of the transgenic embryo into the reproductive tract of a pseudopregnant host mother, usually of the same species. See Wagner, U.S. Pat. No. 4,873,191, Brinster, et al., 1985, Hogan, et al., 1986, Robertson 1987, Pedersen, et al., 1990.

The use of this method to make transgenic livestock is also widely practiced by those of skill in the art. As an example, transgenic swine are routinely produced by the microinjection of a transgene transcription unit into pig embryos. See, for example, PCT Publication No. WO92/11757 In brief, this procedure may, for example, be performed as follows.

First, the transgene transcription unit is gel isolated and extensively purified through, for example, an ELUTIP column (Schleicher & Schuell, Keene, N.H.), dialyzed against pyrogen free injection buffer (10 mM Tris, pH7.4+0.1 mM EDTA in pyrogen free water) and used for embryo injection.

Embryos are recovered from the oviduct of a hormonally synchronized, ovulation induced sow, preferably at the pronuclear stage. They are placed into a 1.5 ml microfuge tube containing approximately 0.5 ml of embryo transfer media (phosphate buffered saline with 10% fetal calf serum). These are centrifuged for 12 minutes at 16,000×g in a microcentrifuge. Embryos are removed from the microfuge tube with a drawn and polished Pasteur pipette and placed into a 35 mm petri dish for examination. If the cytoplasm is still opaque with lipid such that the pronuclei are not clearly visible, the embryos are centrifuged again for an additional 15 minutes. Embryos to be microinjected are placed into a drop of media (approximately 100 µl) in the center of the lid of a 100 mm petri dish. Silicone oil is used to cover this drop and to fill the lid to prevent the medium from evaporating. The petri dish lid containing the embryos is -set onto an inverted microscope equipped with both a heated stage (37.5°–38° C.) and Hoffman modulation contrast optics (200× final magnification). A finely drawn and polished micropipette is used to stabilize the embryos while about 1–2 picoliters of injection buffer containing approximately 200–500 copies of the purified transgene transcription unit is delivered into the nucleus, preferably the male pronucleus, with another finely drawn and polished micropipette. Embryos surviving the microinjection process as judged by morphological observation are loaded into a polypropylene tube (2 mm ID) for transfer into the recipient pseudopregnant sow.

Offspring are tested for the presence of the transgene by isolating genomic DNA from tissue removed from the tail of each piglet and subjecting about 5 micrograms of this genomic DNA to nucleic acid hybridization analysis with a transgene specific probe.

Another commonly used technique for generating transgenic animals involves the genetic manipulation of embryonic stem cells (ES cells) as described in PCT Patent Publication No. WO 93/02188 and Robertson, 1987. In accordance with this technique, ES cells are grown as described in, for example, Robertson, 1987, and in U.S. Pat. No. 5,166,065 to Williams et al. Genetic material is introduced into the embryonic stem cells by, for example, electroporation according, for example, to the method of McMahon, et al., 1990, or by transduction with a retroviral vector according, for example, to the method of Robertson, et al., 1986, or by any of the various techniques described by Lovell-Badge, 1987.

Chimeric animals are generated as described, for example, in Bradley, 1987. Briefly, genetically modified ES cells are introduced into blastocysts and the modified blastocysts are then implanted in pseudo-pregnant female animals. Chimeras are selected from the offspring, for example by the observation of mosaic coat coloration resulting from differences in the strain used to prepare the ES cells and the strain used to prepare the blastocysts, and are bred to produce non-chimeric transgenic animals.

Other methods for the production of transgenic animals are disclosed in U.S. Pat. No. 5,032,407 to Wagner et al., and PCT Publication No. WO90/08832.

Among other applications, transgenic animals prepared in accordance with the invention are useful as model systems for testing the xenotransplantation of their engineered tissues or organs and as sources of engineered tissues or organs for xenotransplantation. The expression of functional TMTCIPs on the surfaces of endothelial cells and/or other cell types in the tissues and organs (e.g., hormone producing cells such as those in the pancreatic islets) of the transgenic animals will provide enhanced protection to those cells, tissues and organs from hyperacute complement-mediated rejection following xenotransplantation in recipient animals, e.g., humans, whose complement can be inhibited by the Ly-6 terminal CIP of the TMTCIP. In addition to their use in producing organs for transplantation, the TMTCIP nucleic acid constructs of the invention can also be used to engineer cultured cells (e.g., endothelial cells) of various species for subsequent use in transplantation.

V. Representative Modifications

Although specific embodiments of the invention are described and illustrated herein, it is to be understood that modifications can be made without departing from the invention's spirit and scope.

For example, the primary amino acid structures of the TMTCIPs of the invention may be modified by creating amino acid substitutions or nucleic acid mutations. At least some complement regulatory activity should remain after such modifications. Similarly, nucleic acid mutations which do not change the amino acid sequences, e.g., third nucleotide changes in degenerate codons, are included within the scope of the invention. Also included are sequences comprising changes that are found as naturally occurring allelic variants of the CIP and TM genes used to create the TMTCIPs.

Without intending to limit it in any manner, the present invention will be more fully described by the following examples.

EXAMPLE 1

Expression Vectors and Retroviral Virion Particles Comprising a CD59/MCP TMTCIP

A transmembrane form of CD59 (CD59-TM) was constructed according to the present invention by replacing the carboxyl-terminal region containing the GPI-anchor signal of CD59 with the carboxyl-terminal region, including the transmembrane domain, of MCP (CD46).

An approximately 314 bp restriction fragment (hereinafter referred to as $CD59_{77}$) containing CD59 truncated at the "truncation-Asn" described above, i.e., amino acid 77 of the mature protein, was prepared by digestion of plasmid pCD59/CCPH (see below) with SspI and BamHI.

The carboxyl-terminus of CD46 was PCR amplified using HeLa cell reverse-transcribed mRNA as template and the following primers: 5'-CGCGAGGCCT ACTTACAAGC CTCCAG-3' (SEQ ID NO:9) and 5'-CGCGCTATTC AGC-CTCTCTG CTCTGC-3' (SEQ ID NO:10). These oligonucleotides amplified a fragment coding for amino acids 270–350 of the mature CD46 protein, a region shown previously to comprise a functional transmembrane domain (Lublin, et al., 1991). The approximately 250 bp fragment produced by this PCR reaction was cloned into a plasmid vector using the T/A cloning kit (Invitrogen, San Diego, Calif.). The pCRII plasmid vector included in this kit served as the recipient, and the resulting plasmid construct was amplified in *E. coli* and purified. The MCP insert was subsequently sequenced to confirm that the plasmid contained the sequence shown in SEQ ID NO:11.

An-endogenous StuI site found at the 5' end of the CD46 PCR fragment was utilized to ligate this domain to the SspI site at the 3' end of $CD59_{77}$ in the eukaryotic expression vector pcDNA3 (Invitrogen, San Diego, Calif.) to yield plasmid pcDNA3/CD59-MCP-TM (ATCC designation 69530).

The resulting construct was linearized with EcoRI, the unpaired ends were filled, and BamHI linkers (#1071, New England Biolabs, Tozer, Mass.) were ligated onto the resulting blunt ends. This Tinkered construct was digested with BamHI and the liberated fragment was subcloned into the BamHI site of the retroviral vector pLXSN (Miller, et al., 1989) to yield pL-CD59-MCP-TM-SN. Constructs with the correct orientation for expression were identified by restriction enzyme analysis and confirmed by sequencing.

A DNA fragment encoding the carboxyl-terminus of the CCPH gene was prepared by PCR amplification using plasmid pKS-/mCCPH (ATCC designation 69178) as template and the following primers: 5'-CCGGACCTGT GTAACTTTAA CGAACAGCTT GAAAATATTG GTAG-GATATG CAATGGAAAT TGTTACAAC-3' (SEQ ID NO:12) and 5'-TAGTTACTGC CCGGACATGC-3' (SEQ ID NO:13). As described above for the MCP PCR fragment, the approximately 250 bp CCPH PCR product was cloned into plasmid pCRII, yielding plasmid pCRII/CCPH, and the CCPH insert was sequenced to confirm that the plasmid contained the desired sequence, in this case SEQ ID NO:14.

The pCRII/CCPH plasmid was then digested with AvaII and EcoRI, and the insert fragment was purified and subcloned in a three-way ligation reaction with plasmid pcDNA/AMP (Invitrogen) cut with BamHI and EcoRI and an approximately 300 base pair BamHI-AvaII fragment isolated from a full length CD59 cDNA construct in pUC19 (Philbrick et al., 1990). The product of this three-way ligation is referred to herein as plasmid pCD59/CCPH.

This plasmid was transfected into Balb/3T3 cells and the cells were assayed for cell surface expression of CD59 epitopes by indirect immunofluorescence as described below in Example 2. As discussed above, the putative TM domain of CCPH contains two cytoplasmic amino acids, within five amino acids of the first cytoplasmic amino acid, that are cysteine residues, a characteristic that is believed to result in low levels of cell surface expression. Cell surface expression of CD59 epitopes was indeed below the levels detectable by the indirect immunofluorescence assay. Control vectors.

Full-length CD59 containing the GPI-anchor signal (CD59-GPI) was cloned into BamHI-EcoRI digested pcDNA3 (Invitrogen) as an BamHI-EcoRI fragment obtained from plasmid pc8-hCD59–103 (ATCC designation 69231) to yield plasmid pcDNA3-CD59-GPI.

Retroviral vector plasmid pL-CD59-GPI-SN was produced by isolating an approximately 1100 bp EcoRI fragment from a full length CD59 cDNA construct in pUC19 (Philbrick et al., 1990) and ligating this fragment into plasmid PLXSN. Constructs with the correct orientation for expression were identified by restriction enzyme analysis. Amphotropic virus production.

Amphotropic virus was produced through an intermediate ecotropic packaging cell line as described in Warren et al., 1987. Briefly, psi 2 cells (obtained from Dr. Stephen L. Warren, Department of Pathology, Yale University School of Medicine, New Haven, Conn.) were transfected with pLXSN or the pLXSN constructs described above, i.e., pL-CD59-MCP-TM-SN or pL-CD59-GPI-SN, using DMSO shock followed by selection in DMEM containing 500 µg/ml (active) G418 and 10% heat inactivated FCS. Transfectants were pooled and a 24 hour supernatant was harvested from the cells at 90% confluency. The ecotropic virus stock was used to infect the amphotropic packaging cell line PA317 (ATCC designation CRL 9078). These cells were also selected in the same medium with G418 following which a virus stock was collected from pooled transductants in the same medium without G418.

EXAMPLE 2

Expression of the CD59/MCP TMTCIP by Mammalian Cells

Cells of the murine fibroblast cell line, Balb/3T3 (ATCC designation CCL 163) were stably transfected with pcDNA3-CD59-GPI, pcDNA3/CD59-MCP-TM, or pcDNA3 alone using the calcium phosphate method (Ausubel, et al., 1992). Cells were selected in DMEM containing 10% heat inactivated FCS and 500 µg/ml of G418 (active) and colonies were isolated using cloning cylinders.

Mouse L cells were obtained from Dr. Peter Cresswell, Immunobiology Department, Yale University School of Medicine, New Haven, Conn. Such mouse L cells are unable to express GPI anchored proteins (Ferguson, et al., 1988). L cells were transduced with the amphotropic virus supernatants obtained using pL-CD59-GPI-SN, pL-CD59-MCP-TM-SN, or PLXSN alone by adding 1 ml of the virus stock to $5 \times 10^5$ L cells in medium containing 8 µg/ml polybrene. After an overnight incubation, medium containing 500 µg/ml G418 was added and selection continued for 14 days. Transduced L cells were selected and analyzed as a pool.

G418 resistant cells were assayed for the presence of CD59 antigens on the cell surface by indirect immunofluorescence using monoclonal and polyclonal antibody preparations. A rabbit polyclonal anti-CD59 antibody preparation, #349, that was produced by injecting rabbits with CD59 purified from human erythrocytes as described by Sims et al., 1989, was provided by Dr. Peter Sims (Blood Research Institute, Milwaukee, Wis.). The anti-CD59 mAb, MEM-43, was purchased from Biodesign International, Kennebunkport, Me.

Cell surface indirect immunofluorescence analysis was typically performed on $2.5 \times 10^5$ cells with 50 µg/ml of the primary polyclonal antibody or 20 µg/ml of the monoclonal antibody in 1xPBS containing 2% fetal bovine serum. Goat anti-rabbit IgG or goat anti-mouse IgG FITC conjugated antisera were used as secondary antibodies (Zymed Laboratories, South San Francisco, Calif.). Fluorescence was measured using a FACSort instrument (Becton-Dickinson Immunocytometry Systems, San Jose, Calif.).

FIG. 2 illustrates cell surface expression profiles of a positive Balb/3T3 clone expressing CD59-TM, as well as of a native human CD59 (CD59-GPI) transfectant as a positive control and a vector (pcDNA3) without insert (vector control) transfectant as a negative control. As shown therein, essentially the same amount of anti-CD59 antibody bound to the surfaces of cells expressing the CD59-TM fusion protein as bound to the positive control cells expressing native CD59. This result shows that equivalent amounts of CD59 antigens were present on the Balb/3T3 cells of the invention (CD59-TM) and those of the positive control (CD59-GPI).

Figure 3:
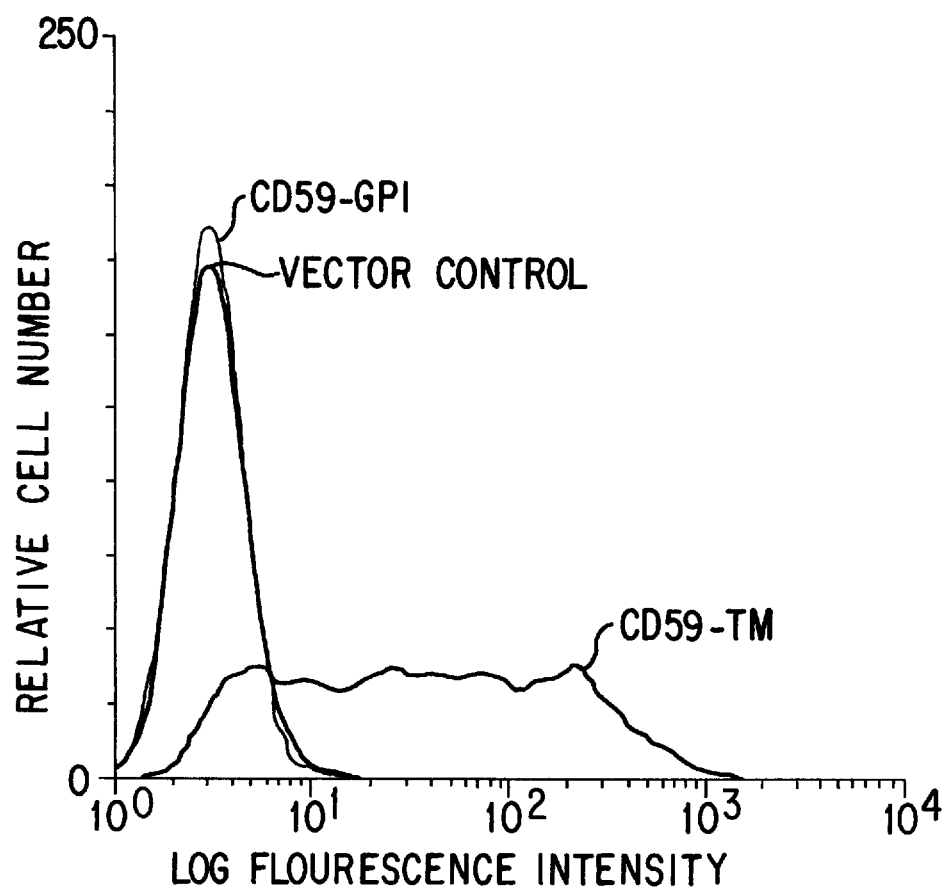
FIG. 3 shows a comparison of the cell surface expression of CD59 epitopes on mouse L cells. The broad trace represents cell surface expression profiles of pooled L cells transduced with retroviral virion particles generated using the pL-CD59-MCP-TM-SN vector (CD59-TM). Also shown are profiles of pooled L cells transduced either with retroviral virion particles generated using the pL-CD59-GPI-SN vector (CD59-GPI) or with retroviral virion particles generated using the pLXSN vector with no insert (Vector Control), as negative controls.

The pooled L cell transfectants showed a wide range of CD59-TM expression while, as expected in cells that cannot express GPI anchored proteins, CD59-GPI was not expressed (FIG. 3).

EXAMPLE 3

Figure 4A:
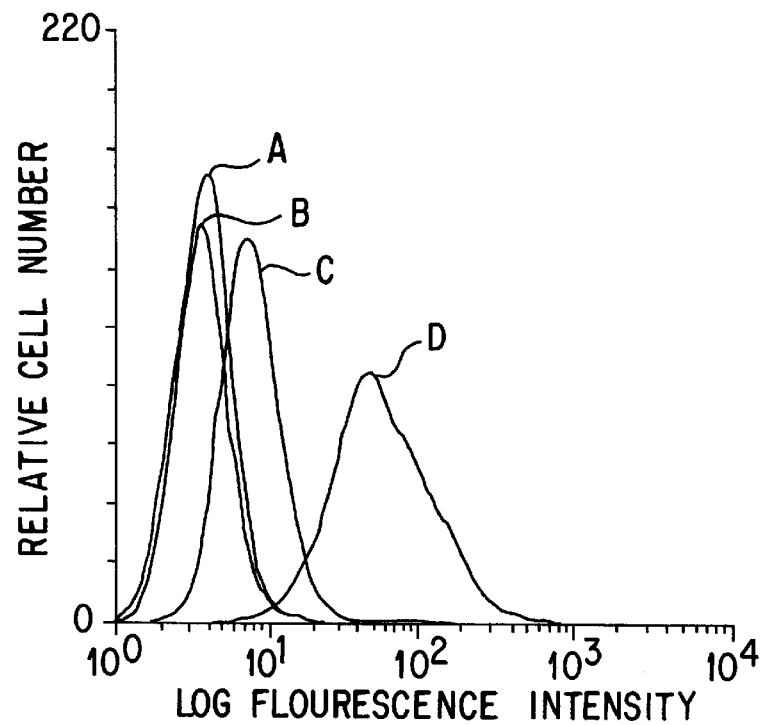
FIG. 4A and 4B shows cell surface levels of CD59 antigens on stably transfected Balb/3T3 cells before and after PI-PLC digestion.
Figure 4B:
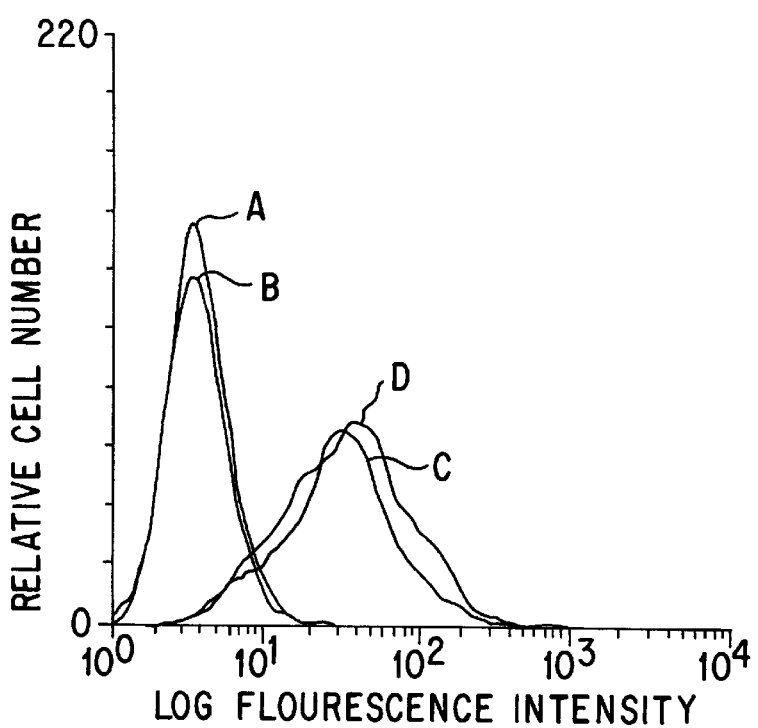

TMTCIP Expressed in Mammalian Cells Is Not Affected By Phosphatidylinositol-Phospholipase C Digestion To test for the presence of a GPI anchor, cells were treated with phosphatidylinositol-phospholipase C (PI-PLC, Boehringer-Mannheim Corporation, Biomedical Products Division, Indianapolis, Indiana) at 1 U/ml for 1 hr at 37° C. prior to FACS analysis. This treatment hydrolyzes (cleaves) GPI anchors, and thus frees GPI anchored proteins from the cell surface. PI-PLC digestion was performed on Balb/3T3 cells expressing the CD59-TM TMTCIP (or CD59-GPI as a control). The results of these experiments are presented in FIG. 4. In these experiments, mock treated cells (no PI-PLC) retained the TMTCIP and native CD59 on their cell surfaces (see curve D in FIG. 4A and FIG. 4B), whereas PI-PLC treatment resulted in the loss of cell surface CIPs from the native CD59 control cells (see curve C in FIG. 4A), but not the CD59-TM cells (see curve C in FIG. 4B). These experiments demonstrate that CD59-TM is not anchored to the cell membrane through a GPI linkage and that CD59-TM is substantially resistant to the action of lipase enzymes which can cleave a glycosyl- phosphatidylinositol (GPI) anchor.

EXAMPLE 4

Functional Analysis of CD59-TM in Mouse Cells

The functional activity of TMTCIP molecules expressed in transfected mouse Balb/3T3 cells and transduced mouse L cells was assessed by a dye release assay that consisted of measuring the efflux of molecules from the cytoplasm, specifically the cytoplasmic indicator dye, Calcein AM (Molecular Probes, Inc., Eugene, Oreg.).

Transfected cells expressing the CD59-TM TMTCIP, as well as cells transfected with the parent expression vectors without CD59-TM encoding inserts (as controls), were grown to confluency in 96-well plates. Cells were washed twice with 200 $\mu$l of Hank's balanced salts solution containing 10 mg/ml bovine serum albumin (HBSS/BSA).

Calcein AM was added (10 $\mu$M final) and the plates were incubated at 37° C. for 30 minutes to allow the dye to be internalized by the cells and converted by cellular esterases into a polar fluorescent derivative that is retained inside undamaged cells. The wells were then washed twice with HBSS/BSA to remove dye remaining outside the cells. The cells were then incubated with anti-Balb/3T3 IgG (2 mg/ml in HBSS/BSA), which served as an activator of the classical complement pathway. After a 30 minute incubation at 23° C., unbound IgG was washed away.

The cells were then incubated at 37° C. for 30 minutes in the presence of human C8 deficient serum supplemented with purified C8 and C9 to allow complement-mediated damage to occur. Human C8 depleted serum, as well as purified C8 and C9, were obtained from Quidel Corporation, San Diego, Calif. The medium bathing the cells was then -transferred to a clean 96-well plate for fluorescence measurement.

Under the conditions of this assay, the fluorescent polar derivative of Calcein AM is only released into the medium bathing the test cells if the integrity of the cell membranes is compromised. Therefore, the fluorescence of the Calcein AM released into the medium bathing the test cells versus that retained in the cells provides an indirect, but accurate measure of the level of complement-mediated damage sustained by the cells. Remaining cell-associated dye was determined from a 1% SDS lysate of the cells retained in the 96-well culture plates. This allowed the calculation of percent dye release using the following formulas: Total= released+retained, and, % release=(released total)×100. Fluorescence was measured using a Millipore CYTOFLUOR 2350 fluorescence plate reader (490 nm excitation, 530 nm emission).

Figure 5:
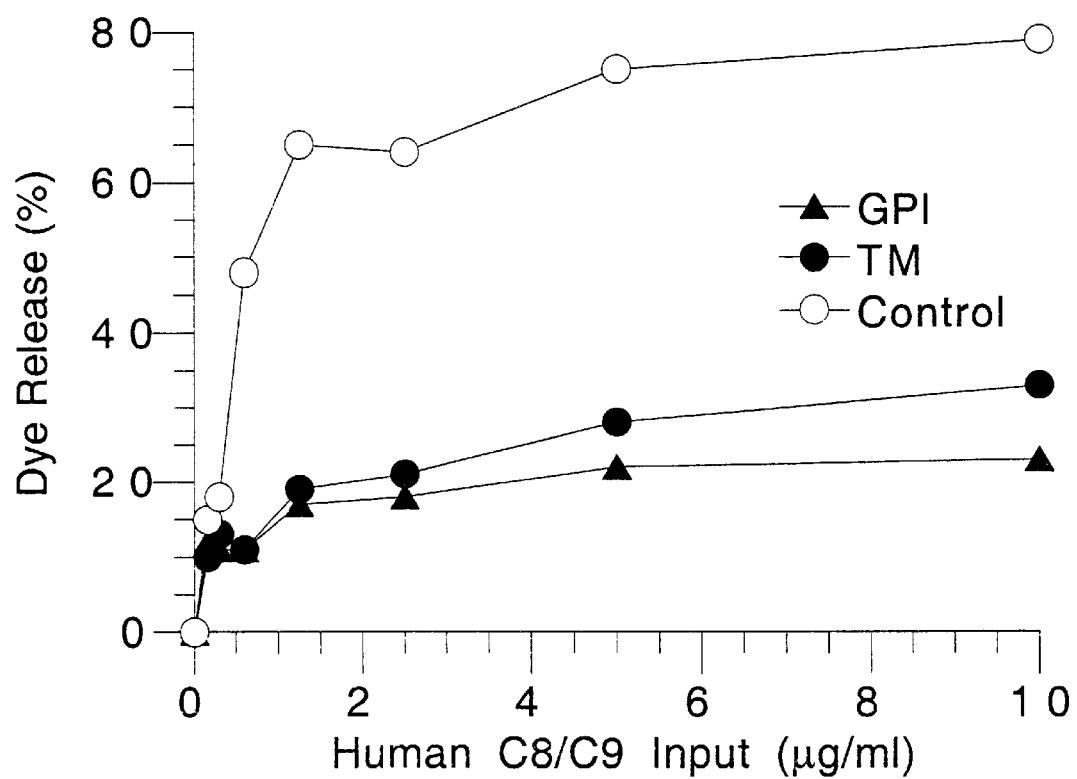
FIG. 5 shows data obtained from dye release assays performed using the transfected Balb/3T3 cells employed in obtaining the data of FIG. 2 and FIG. 4. The cells were challenged with 20% human C8 depleted serum supplemented with a mixture of equal parts of purified human C8 and C9. The amounts, in micrograms per milliliter final concentration, of the mixture of human C8 and C9 added are indicated on the abscissa and the percent of dye release is indicated on the ordinate.

The dye release assays showed that for transfected Balb/3T3 clones expressing equivalent levels of CD59-GPI or CD59-TM (FIG. 2), CD59-TM provided a level of protection from complement attack equivalent to that afforded by the native, GPI-anchored, CD59-GPI molecule (FIG. 5) In particular, cells expressing either of these molecules were approximately 3-fold more effective in preventing complement-mediated lysis at 2.5 $\mu$g/ml C8/C9 than cells transfected with the pcDNA3 vector alone, which were readily lysed.

These results demonstrate that 1) CD59-TM can be stably expressed on the surface of Balb/3T3 cells, and 2) this chimeric molecule has comparable function to native CD59. The retention of wild-type levels of complement regulatory activity by CD59-TM is of considerable significance in that it shows that the functionality of the CD59 molecule is not substantially altered by truncation coupled with addition of a TM domain. This result could not have been predicted in advance, especially since other alterations of the CD59 molecule, e.g., truncation of the carboxyl-terminus without addition of a TM domain, or alterations of single amino acids, have been shown to produce molecules with substantially altered expression and/or functionality. See, for example, Nakano, et al., 1993; Norris, et al., 1993; and Petranka, et al., 1993.

Figure 6:
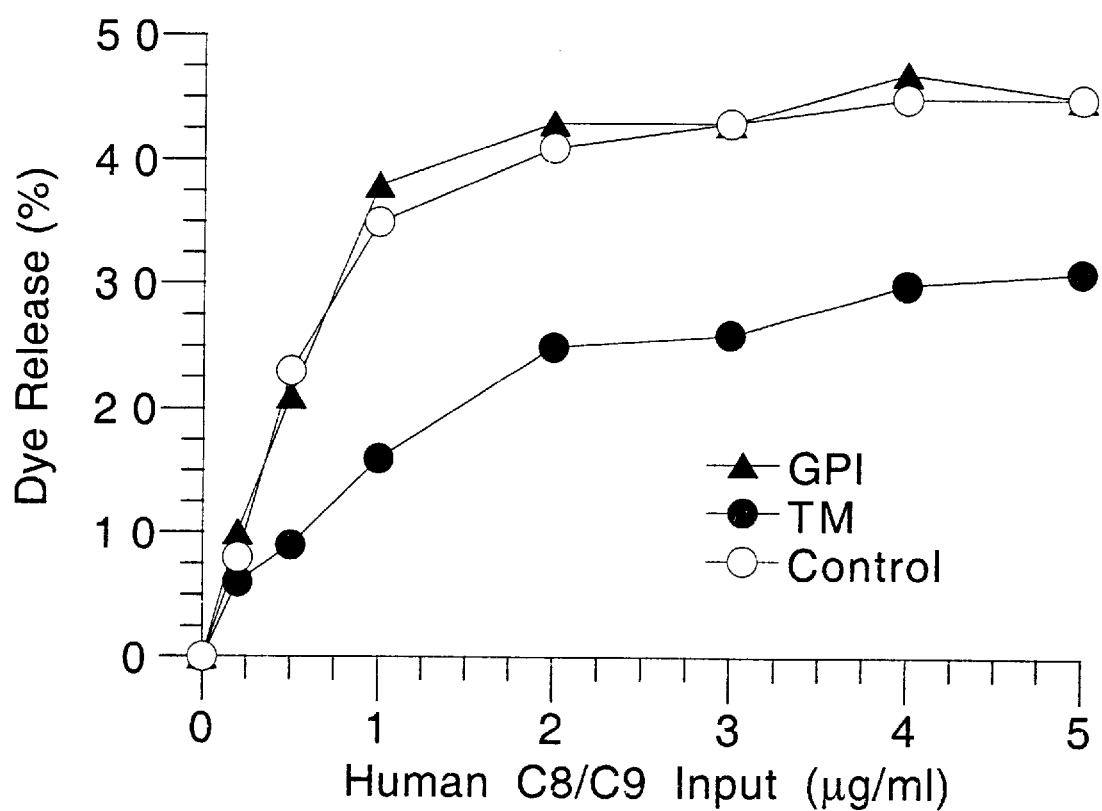
FIG. 6 shows data obtained from dye release assays performed using the transfected mouse L cells employed in obtaining the data of FIG. 3. The cells were challenged with 20% human C8 depleted serum supplemented with a mixture of equal parts of purified human C8 and C9. The amounts, in micrograms per milliliter final concentration, of the mixture of human C8 and C9 added are indicated on the abscissa and the percent of dye release is indicated on the ordinate.

Dye release assays were also performed on mouse L cells transduced with the retroviral virion particles generated using the pL-CD59-MCP-TM-SN vector, the pL-CD59-GPI-SN vector, or the no insert PLXSN vector. The results of these experiments are presented in FIG. 6. Only L cells transduced with retroviral particles generated using pL-CD59-MCP-TM-SN demonstrated substantial protection against complement attack. These results demonstrate that the chimeric CD59-TM molecule can successfully be expressed in a cell line unable to express GPI-anchored proteins and that the molecule functions to protect the cells from complement lysis.

The foregoing results show that CD59 retains its Ly-6 terminal complement inhibitor activity when anchored to the cell membrane by a heterologous transmembrane domain, rather than a GPI anchor. This fundamental result, in combination with the conserved nature of all known Ly-6 terminal complement inhibitor proteins (see U.S. patent application Ser. No. 08/105,735 (now abandoned) and PCT patent application Ser. No. PCT/US93/006772), indicates that a heterologous transmembrane domain can be substituted for the GPI signal sequence of a Ly-6 terminal complement inhibitor protein without substantially altering the complement inhibitor activity of the protein.

In comparison to using a native Ly-6 terminal CIP, the TMTCIPs of the invention have the advantages that they cannot produce cell activation of the type which depends on the presence of the GPI anchor of the native Ly-6 terminal CIP, and that they cannot be removed from the cell surface by the action of phospholipase enzymes and are less prone to vesicular shedding. These advantages make the TMTCIPs of the invention more suitable than native Ly-6 terminal CIPs for various medical applications, including the facilitation of transplantation of xenogenetic organs.

Although preferred and other embodiments of the invention have been described herein, other embodiments, including a variety of modifications may be perceived and practiced by those skilled in the art without departing from the scope of the invention. For example, the primary amino acid structures of the fusion proteins of the invention may be modified by creating amino acid mutants. Such mutants should retain more than 50% of the complement regulatory activity of the parent terminal CIP. Other modifications and variations include forming derivatives of the fusion protein to include covalent or aggregated conjugates of the protein or its fragments with other proteins or polypeptides. The following claims are intended to cover the specific embodiments set forth herein as well as such modifications, variations, and equivalents.

Throughout this application, various publications, patents, and patent applications have been referred to. The teachings and disclosures of these publications, patents, and patent applications in their entireties are hereby incorporated by reference into this application to more fully describe the state of the art to which the present invention pertains.

DEPOSITS

Plasmids pcDNA3/CD59-MCP-TM, pc8-hCD59–103, and pKS-/mCCPH, discussed above, have been deposited with the American Type Culture Collection, 12301 Parklawn Drive, Rockville, Md., 20852, United States of America, in E. coli and have been assigned the designations 69530, 69231, and 69178, respectively. These deposits were made under the Budapest Treaty on the International Recognition of the Deposit of Micro-organisms for the Purposes of Patent Procedure (1977).

References

Ausubel, et al., eds., "Current Protocols in Molecular Biology", Wiley Interscience, John Wiley and Sons, New York, 1992.
Albrecht, et al., 1992. Virology. 190:527–530.
Bhakdi, et al., 1991. Immunol. Today. 12: 318–321.
Bradley. in Robertson. ed. "Teratocarcinomas and Embryonic Stem Cells a Practical Approach" IRL Press, Eynsham, Oxford, England, 1987.
Branden, et al., "Introduction to Protein Structure" Garland Publishing, Inc., New York, 1991.
Brasile, et al., 1985. Transplantation. 40:672–675.
Brasile, et al., 1987. Trans. Proceed. 19:894–895.
Brinster, et al., 1985. Proc. Natl. Acad. Sci. USA. 82:4438–4442.
Brown,iet al., 1992. Cell. 68:533–544.
Butikofer, et al., 1989. Blood. 74:1481–1485.
Card, et al., 1991. J. Immunol. 146:4092–4098.
Cinek, et al., 1992. J. Immunol. 149:2262–2270.
Cosset, et al., 1990. J. Virol. 64:1070–1078.
Dalmasso, et al., 1992. Am. J. Pathol. 140:1157–1166.
Davies, et al., 1989. J. Exp. Med. 170:637–654.
Davitz, et al., 1987. Science. 238:81–84.
Deckert, et al., 1992. J. Immunol. 148:672–677.
Eglitis, et al., 1988. Biotechniques. 6:608–614.
Eikelenboom, et al., 1989. Virchow's Archiv. B. Cell. Pathol. 56:259–262.
Engelman, et al., 1986. Annu. Rev. Biophys. Biophys. Chem. 15:321–353.
Esser. 1991. Immunol. Today. 12:316–318.
Ferguson, et al., 1988. Ann. Rev. Biochem. 57:285–320.
Groux, et al., 1989. J. Immunol. 142:3013–3020.
Gumley, et al., 1992. J. Immunol. 149:2615–2618.
Harada, et al., 1990. J. Immunol. 144:1823–1828.
Hogan, et al., in "Manipulating the Mouse Embryo: A Laboratory Manual". Cold Spring Harbor Laboratory, Cold Spring Harbor, N.Y., 1986.
Holguin, et al., 1989. J. Clin. Invest. 84:7–17.
Korman, et al., 1987, Proc. Natl. Acad. Sci. USA. 84:2150–2154.
Kyte, et al., 1982. J. Mol. Biol. 157:105.
Lovell-Badge. in Robertson. ed. "Teratocarcinomas and Embryonic Stem Cells a Practical Approach" IRL Press, Eynsham, Oxford, England, 1987.
Lublin, et al., 1991. J. Exp. Med. 174:35–44.
Markowitz, et al., 1988. J. Virol. 62:1120–1124.
McMahon, et al., 1989. Cell. 58:1075–1084.
McMahon, et al., 1990 Cell. 62:1073–1085.
Meri, et al., 1990. Immunology. 70:1–9.
Miller, et al., 1986. Mol. Cell Biol. 6:2895–2902.
Miller, et al., 1989. Biotechniques. 7:981–990.
Moran, et al., 1992. J. Immunol. 140:1736–1743.
Morgenstern, et al., 1990. Nucleic Acids Res. 18:3587–3596.
Nakano, et al., 1993. Molec. Immunol. 30(suppl. 1) :37.
Norris, et al., 1993. Blood. 82(Suppl.):202a.
Nose, et al., 1990. Immunology. 70: 145–149.
Okada, et al., 1989a. Biochem. Biophys. Res. Commun. 162: 1553–1559.
Okada, et al., 1989b. J. Immunol. 143:2262–2266.
Pedersen, et al., 1990. "Transgenic Techniques in Mice—A Video Guide", Cold Spring Harbor Laboratory, Cold Spring Harbor, N.Y.
Petranka, et al., 1992. Proc. Natl. Acad. Sci. USA. 89:7876–7879.
Petranka, et al., 1993. Molec. Immunol. 30(suppl. 1):44.
Philbrick, et al., 1990. Eur. J. Immunol. 20:87–92.
Purcell, et al., 1991. Immunogenetics 33:335–344.
Robertson, et al., 1986. Nature. 323:445–448.
Robertson. 1987. in Robertson. ed. "Teratocarcinomas and Embryonic Stem Cells a Practical Approach" IRL Press, Eynsham, Oxford, England.
Roldan, et al., 1990. EMBO J. 9:467–474.
Rollins, et al., 1990. J. Immunol. 144:3478–3483.
Rollins, et al., 1991. J. Immunol. 146:2345–2351.
Rother, et al., 1994. J. Virol. 68:730–737.
Sambrook, et al., Molecular cloning: a laboratory manual. Second Edition. Cold Spring Harbor Laboratory Press, Cold Spring Harbor, N.Y. 1989.
Sandrin, et al., 1993. Proc. Natl. Acad. Sci. USA. 90:11391.
Sawada, et al., 1989. DNA Cell. Biol. 9:213–220.
Schonermark, et al., 1986. J. Immunol. 136:1772.
Seaman, et al., 1991. J. Exp. Med. 173:251–260.
Shevach, et al., 1989. Immunol. Today. 10:195–200.
Sims, et al., 1989. J. Biol. Chem. 264:19228–19235.
Starzl, et al., 1993. Lancet. 341:65–71.
Stefanova, et al., 1989. Mol. Immunol. 26:153–161.
Stefanova, et al., 1991. J. Immunol. 147:1587–1592.
Su, et al., 1991. J. Cell Biol. 112:377–384.
Sugita, et al., 1988. J. Biochem. 104:633–637.
Suter, et al., 1992. J. Neurosci. 12:306–318.
Talib, et al., 1991. Gene. 98:289–293.
Tone, et al., 1992. J. Mol. Biol. 227:971–976.
Vakeva, et al., 1992. Lab. Invest. 67:608–616.
Venneker, et al., 1992. Exp. Clin. Immunogenet. 9:33–47.
Walsh, et al., 1991. Eur. J. Immunol. 21:847–850.
Warren, et al., 1987. Mol. Cell Biol. 7:1326–1332.
Whitlow, et al., 1990. Cell Immunol. 126:176–184.
Whitlow, et al., 1993. Blood. 81:510–516.
Williams, et al., 1988. Immunogenetics. 27:265–272.
Wing, et al., 1992. Immunology. 76:140–145.
Yamada, et al., 1990. Neurosci. Lttrs. 112:161–166.
Zalman, et al., 1986. Proc. Natl. Acad. Sci. USA. 83:6975–6979.
Zhao, et al., 1991. J. Biol. Chem. 266:13418–13422.

What is claimed is:

1. A chimeric protein comprising:

(i) a first polypeptide region comprising a portion of a parent Ly-6 terminal complement inhibitor protein, said portion including a complete Ly-6 motif and not including an operative signal sequence directing the attachment of a glycosyl-phosphatidylinositol (GPI) anchor; and (ii) a second polypeptide region linked to the first polypeptide region, said second polypeptide region comprising a transmembrane domain from a heterologous protein, wherein said chimeric protein has complement inhibitory activity against human complement.

2. The chimeric protein of claim 1 wherein said protein has greater than 50% of the complement inhibitory activity of the parent LV-6 terminal complement inhibitor protein.

3. The chimeric protein of claim 1 wherein the portion of the parent Ly-6 terminal complement inhibitor protein comprises said parent protein minus all or less than all of the amino acid residues downstream of its Ly-6 motif.

4. The chimeric protein of claim 1 wherein the parent terminal complement inhibitor is CD59 and the heterologous protein is CD46.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 763 base pairs
        ( B ) TYPE: Nucleic Acid
        ( C ) STRANDEDNESS: Double
        ( D ) TOPOLOGY: Linear ( i i ) MOLECULE TYPE: cDNA to mRNA
        ( A ) DESCRIPTION: BABCIP full length cDNA ( i i i ) HYPOTHETICAL: No ( i v ) ANTI-SENSE: No ( v i ) ORIGINAL SOURCE:
        ( A ) ORGANISM: Papio hamadryas ( v i i ) IMMEDIATE SOURCE:
        ( A ) LIBRARY: Baboon Spleen Lambda ZAPII cDNA Library, Catalog
            #    936103, Stratagene Cloning Systems,La Jolla, California ( x i ) SEQUENCE DESCRIPTION: SEQ ID NO:1:

```
GGTTATGTGC  CCACACTTGC  CTAGGCTGTG  AATAGTTAGT  ACCTCTGATT                    50

ACTTAGTTAA  ATATGCTTCT  AGATGAGAAG  TAGCGAAAGG  CTGGAAGGGA                   100

TCCCGGGCGC  CGCCAGGTTC  TGTGGACAAT  CACA  ATG  GGA                           140
                                         Met  Gly
                                         -25

ATC  CAA  GGA  GGG  TCT  GTC  CTG  TTC  GGG  CTG  CTG  CTT  GTC  CTG  GCT   185
Ile  Gln  Gly  Gly  Ser  Val  Leu  Phe  Gly  Leu  Leu  Leu  Val  Leu  Ala
          -20                      -15                           -10

GTC  TTC  TGC  CAT  TCA  GGT  CAT  AGC  CTG  CAG  TGC  TAC  AAC  TGT  CCT   230
Val  Phe  Cys  His  Ser  Gly  His  Ser  Leu  Gln  Cys  Tyr  Asn  Cys  Pro
               -5                        1                    5

AAC  CCA  ACT  ACT  GAC  TGC  AAA  ACA  GCC  ATC  AAT  TGT  TCA  TCT  GGT   275
Asn  Pro  Thr  Thr  Asp  Cys  Lys  Thr  Ala  Ile  Asn  Cys  Ser  Ser  Gly
          10                        15                          20

TTT  GAT  ACG  TGT  CTC  ATT  GCC  AGA  GCT  GGG  TTA  CAA  GTA  TAT  AAC   320
Phe  Asp  Thr  Cys  Leu  Ile  Ala  Arg  Ala  Gly  Leu  Gln  Val  Tyr  Asn
          25                        30                          35

CAG  TGT  TGG  AAG  TTT  GCG  AAT  TGC  AAT  TTC  AAT  GAC  ATT  TCA  ACC   365
Gln  Cys  Trp  Lys  Phe  Ala  Asn  Cys  Asn  Phe  Asn  Asp  Ile  Ser  Thr
          40                        45                          50

CTC  TTG  AAG  GAA  AGC  GAG  CTA  CAG  TAC  TTC  TGC  TGC  AAG  AAG  GAC   410
Leu  Leu  Lys  Glu  Ser  Glu  Leu  Gln  Tyr  Phe  Cys  Cys  Lys  Lys  Asp
          55                        60                          65

CTG  TGT  AAC  TTT  AAC  GAA  CAG  CTT  GAA  AAT  GGT  GGG  ACA  TCC  TTA   455
Leu  Cys  Asn  Phe  Asn  Glu  Gln  Leu  Glu  Asn  Gly  Gly  Thr  Ser  Leu
          70                        75                          80

TCA  GAG  AAA  ACA  GTT  GTT  CTG  CTG  GTG  ACC  CTA  CTT  CTG  GCA  GCA   500
Ser  Glu  Lys  Thr  Val  Val  Leu  Leu  Val  Thr  Leu  Leu  Leu  Ala  Ala
          85                        90                          95

GCC  TGG  TGC  CTT  CAT  CCC  TAAGTCAACA  CCAGGAGAGC  TTCTCCCATA             548
Ala  Trp  Cys  Leu  His  Pro
          100

CTCCCCGTTC  CTGCGTAGTC  CCCTTTCCCT  CGTGCNGATT  CTAAAGGCTT                   598

ATATTTTCCA  ACCGGATCCT  GTTGGGAAAG  AATAAAATTG  ACTTGAGCAA                   648

CCTGGCTAAG  ATAGAGGGGC  TCTGGAAGAC  TTCGAAGACC  AGTCCTGTTT                   698
```

| GCAGGGAAGC | CCCACTTGAA | GGAAGAAGTT | TAAGAGTGAA | GTAGGTGTGA | 748 |

| CTTGAGCTAG | ATTGG | | | | 763 |

(2) INFORMATION FOR SEQ ID NO:2:

(i) SEQUENCE CHARACTERISTICS:
        (A) LENGTH: 469 base pairs
        (B) TYPE: Nucleic Acid
        (C) STRANDEDNESS: Double
        (D) TOPOLOGY: Linear (ii) MOLECULE TYPE: cDNA to mRNA
        (A) DESCRIPTION: AGMCIP full length cDNA (iii) HYPOTHETICAL: No (iv) ANTI-SENSE: No (vi) ORIGINAL SOURCE:
        (A) ORGANISM: Cercopithecus aethiops
        (H) CELL LINE: COS-1 (ATCC CRL 1650)

(xi) SEQUENCE DESCRIPTION: SEQ ID NO:2:

```
                                   TTCTGTGGAC AATCACA ATG GGA ATC          26
                                                       Met Gly Ile
                                                       -25

CAA GGA GGG TCT GTC CTG TTC GGG CTG CTG CTT GCC CTG GCT GTC                71
Gln Gly Gly Ser Val Leu Phe Gly Leu Leu Leu Ala Leu Ala Val
        -20                 -15                 -10

TTC TGC CAT TCA GGT CAT AGC CTG CAA TGC TAC AAC TGT CCT AAC                116
Phe Cys His Ser Gly His Ser Leu Gln Cys Tyr Asn Cys Pro Asn
         -5              1                   5

CCA ACT ACT AAC TGC AAA ACA GCC ATC AAT TGT TCA TCT GGT TTT                161
Pro Thr Thr Asn Cys Lys Thr Ala Ile Asn Cys Ser Ser Gly Phe
     10              15                  20

GAT ACG TGT CTC ATT GCC AGA GCT GGG TTA CAA GTA TAT AAC CAG                206
Asp Thr Cys Leu Ile Ala Arg Ala Gly Leu Gln Val Tyr Asn Gln
     25              30                  35

TGT TGG AAG TTT GCG AAT TGC AAT TTC AAT GAC ATT TCA ACC CTC                251
Cys Trp Lys Phe Ala Asn Cys Asn Phe Asn Asp Ile Ser Thr Leu
     40              45                  50

TTG AAG GAA AGC GAG CTA CAG TAC TTC TGC TGC AAG GAG GAC CTG                296
Leu Lys Glu Ser Glu Leu Gln Tyr Phe Cys Cys Lys Glu Asp Leu
     55              60                  65

TGT AAC GAA CAG CTT GAA AAT GGT GGG ACA TCC TTA TCA GAG AAA                341
Cys Asn Glu Gln Leu Glu Asn Gly Gly Thr Ser Leu Ser Glu Lys
     70              75                  80

ACA GTT CTT CTG CTG GTG ACC CCA CTT CTG GCA GCA GCC TGG TGC                386
Thr Val Leu Leu Leu Val Thr Pro Leu Leu Ala Ala Ala Trp Cys
     85              90                  95

CTT CAT CCC TAAGTCAACA CCAGGAGAGC TTCTCCATA CTCCCGTTC                      435
Leu His Pro
     100

CTGCGTAGTC CCCTTTCCCC GGCCGCATTC TAAA                                      469
```

(2) INFORMATION FOR SEQ ID NO:3:

(i) SEQUENCE CHARACTERISTICS:
        (A) LENGTH: 396 base pairs
        (B) TYPE: Nucleic Acid
        (C) STRANDEDNESS: Double
        (D) TOPOLOGY: Linear (ii) MOLECULE TYPE: cDNA to mRNA
        (A) DESCRIPTION: SQMCIP full coding cDNA (  i i i  ) HYPOTHETICAL: No (  i v  ) ANTI-SENSE: No (  v i  ) ORIGINAL SOURCE:
    ( A ) ORGANISM: Saimiri sciureus
    ( H ) CELL LINE: DPSO 114/74 (ATCC CCL 194)

(  x i  ) SEQUENCE DESCRIPTION: SEQ ID NO:3:

```
ATG  GGA  ATC  CAA  GGA  GGG  TCT  GTC  CTG  TTT  GGG  CTG  CTG  CTC  GTC         45
Met  Gly  Ile  Gln  Gly  Gly  Ser  Val  Leu  Phe  Gly  Leu  Leu  Leu  Val
-25                      -20                      -15

CTG  GCT  GTC  TTC  TGC  CAT  TCA  GGT  AAT  AGC  CTG  CAA  TGC  TAC  AGC         90
Leu  Ala  Val  Phe  Cys  His  Ser  Gly  Asn  Ser  Leu  Gln  Cys  Tyr  Ser
-10                      -5                        1                     5

TGT  CCT  CTC  CCA  ACC  ATG  GAG  TCC  ATG  GAG  TGC  ACT  GCG  TCC  ACC        135
Cys  Pro  Leu  Pro  Thr  Met  Glu  Ser  Met  Glu  Cys  Thr  Ala  Ser  Thr
                     10                       15                          20

AAC  TGT  ACA  TCT  AAT  CTT  GAT  TCG  TGT  CTC  ATT  GCC  AAA  GCC  GGG        180
Asn  Cys  Thr  Ser  Asn  Leu  Asp  Ser  Cys  Leu  Ile  Ala  Lys  Ala  Gly
                     25                       30                          35

TCA  GGA  GTA  TAT  TAC  CGG  TGT  TGG  AAG  TTT  GAC  GAT  TGC  AGT  TTC        225
Ser  Gly  Val  Tyr  Tyr  Arg  Cys  Trp  Lys  Phe  Asp  Asp  Cys  Ser  Phe
                     40                       45                          50

AAA  CGC  ATC  TCA  AAC  CAA  TTG  TCG  GAA  ACT  CAG  TTA  AAG  TAT  CAC        270
Lys  Arg  Ile  Ser  Asn  Gln  Leu  Ser  Glu  Thr  Gln  Leu  Lys  Tyr  His
                     55                       60                          65

TGC  TGC  AAG  AAG  AAC  CTG  TGT  AAT  GTT  AAG  GAA  GTG  CTT  GAA  AAT        315
Cys  Cys  Lys  Lys  Asn  Leu  Cys  Asn  Val  Lys  Glu  Val  Leu  Glu  Asn
                     70                       75                          80

GGT  GGG  ACA  ACC  TTA  TCA  AAG  AAA  ACA  ATT  CTT  CTG  CTG  GTG  ACC        360
Gly  Gly  Thr  Thr  Leu  Ser  Lys  Lys  Thr  Ile  Leu  Leu  Leu  Val  Thr
                     85                       90                          95

CCG  TTT  CTG  GCA  GCA  GCC  TGG  AGC  CGT  CAT  CCC  TAA                       396
Pro  Phe  Leu  Ala  Ala  Ala  Trp  Ser  Arg  His  Pro
                    100
```

( 2 ) INFORMATION FOR SEQ ID NO:4:

( i ) SEQUENCE CHARACTERISTICS:
        ( A ) LENGTH: 387 base pairs
        ( B ) TYPE: Nucleic Acid
        ( C ) STRANDEDNESS: Double
        ( D ) TOPOLOGY: Linear ( i i ) MOLECULE TYPE: cDNA to mRNA
        ( A ) DESCRIPTION: OWMCIP full coding cDNA ( i i i ) HYPOTHETICAL: No ( i v ) ANTI-SENSE: No ( v i ) ORIGINAL SOURCE:
        ( A ) ORGANISM: Aotus trivirgatus
        ( H ) CELL LINE: OMK (ATCC CRL 1556)

( x i ) SEQUENCE DESCRIPTION: SEQ ID NO:4:

```
ATG  GGA  ATT  CAA  GGA  GGG  TCT  GTC  CTG  TTT  GGG  CTG  CTG  CTC  GTC         45
Met  Gly  Ile  Gln  Gly  Gly  Ser  Val  Leu  Phe  Gly  Leu  Leu  Leu  Val
-25                      -20                      -15

CTG  GCT  GTC  TTC  TGC  CAT  TCA  GGT  AAT  AGC  CTG  CAG  TGC  TAC  AGC         90
Leu  Ala  Val  Phe  Cys  His  Ser  Gly  Asn  Ser  Leu  Gln  Cys  Tyr  Ser
-10                      -5                        1                     5

TGT  CCT  TAC  CCA  ACC  ACT  CAG  TGC  ACT  ATG  ACC  ACC  AAC  TGT  ACA        135
Cys  Pro  Tyr  Pro  Thr  Thr  Gln  Cys  Thr  Met  Thr  Thr  Asn  Cys  Thr
                     10                       15                          20
```

| | | | | | | | | | | | | | | | |
|---|---|---|---|---|---|---|---|---|---|---|---|---|---|---|---|
| TCT | AAT | CTT | GAT | TCG | TGT | CTC | ATT | GCC | AAA | GCC | GGG | TCA | CGA | GTA | 180 |
| Ser | Asn | Leu | Asp | Ser | Cys | Leu | Ile | Ala | Lys | Ala | Gly | Ser | Arg | Val | |
| | | | | 25 | | | | | 30 | | | | | 35 | |
| TAT | TAC | CGG | TGT | TGG | AAG | TTT | GAG | GAT | TGC | ACT | TTC | AGC | CGC | GTT | 225 |
| Tyr | Tyr | Arg | Cys | Trp | Lys | Phe | Glu | Asp | Cys | Thr | Phe | Ser | Arg | Val | |
| | | | | 40 | | | | | 45 | | | | | 50 | |
| TCA | AAC | CAA | TTG | TCT | GAA | AAT | GAG | TTA | AAG | TAT | TAC | TGC | TGC | AAG | 270 |
| Ser | Asn | Gln | Leu | Ser | Glu | Asn | Glu | Leu | Lys | Tyr | Tyr | Cys | Cys | Lys | |
| | | | | 55 | | | | | 60 | | | | | 65 | |
| AAG | AAC | CTG | TGT | AAC | TTT | AAT | GAA | GCG | CTT | AAA | AAT | GGT | GGG | ACA | 315 |
| Lys | Asn | Leu | Cys | Asn | Phe | Asn | Glu | Ala | Leu | Lys | Asn | Gly | Gly | Thr | |
| | | | | 70 | | | | | 75 | | | | | 80 | |
| ACC | TTA | TCA | AAG | AAA | ACA | GTC | CTC | CTG | GTG | ATC | CCA | TTT | CTG | | 360 |
| Thr | Leu | Ser | Lys | Lys | Thr | Val | Leu | Leu | Leu | Val | Ile | Pro | Phe | Leu | |
| | | | | 85 | | | | | 90 | | | | | 95 | |
| GTA | GCA | GCC | TGG | AGC | CTT | CAT | CCC | TAA | | | | | | | 387 |
| Val | Ala | Ala | Trp | Ser | Leu | His | Pro | | | | | | | | |
| | | | | 100 | | | | | | | | | | | |

( 2 ) INFORMATION FOR SEQ ID NO:5:

( i ) SEQUENCE CHARACTERISTICS:
        ( A ) LENGTH: 387 base pairs
        ( B ) TYPE: Nucleic Acid
        ( C ) STRANDEDNESS: Double
        ( D ) TOPOLOGY: Linear ( i i ) MOLECULE TYPE: cDNA to mRNA
        ( A ) DESCRIPTION: MARCIP full coding cDNA ( i i i ) HYPOTHETICAL: No ( i v ) ANTI-SENSE: No ( v i ) ORIGINAL SOURCE:
        ( A ) ORGANISM: Saguinus nigricollis
        ( H ) CELL LINE: 1283.Lu (ATCC CRL 6297)

( x i ) SEQUENCE DESCRIPTION: SEQ ID NO:5:

| | | | | | | | | | | | | | | | |
|---|---|---|---|---|---|---|---|---|---|---|---|---|---|---|---|
| ATG | GGA | ATC | CAA | GGA | GGG | TCT | GTC | CTG | TTT | GGG | CTG | CTG | CTC | ATC | 45 |
| Met | Gly | Ile | Gln | Gly | Gly | Ser | Val | Leu | Phe | Gly | Leu | Leu | Leu | Ile | |
| -25 | | | | -20 | | | | | -15 | | | | | | |
| CTG | GCT | GTC | TTC | TGC | CAT | TCA | GGT | CAT | AGC | CTG | CAG | TGC | TAC | AGC | 90 |
| Leu | Ala | Val | Phe | Cys | His | Ser | Gly | His | Ser | Leu | Gln | Cys | Tyr | Ser | |
| -10 | | | | -5 | | | | | 1 | | | | | 5 | |
| TGT | CCT | TAC | TCA | ACC | GCT | CGG | TGC | ACT | ACG | ACC | ACC | AAC | TGT | ACA | 135 |
| Cys | Pro | Tyr | Ser | Thr | Ala | Arg | Cys | Thr | Thr | Thr | Thr | Asn | Cys | Thr | |
| | | | | 10 | | | | | 15 | | | | | 20 | |
| TCT | AAT | CTT | GAT | TCA | TGT | CTC | ATT | GCC | AAA | GCC | GGG | TTA | CGA | GTA | 180 |
| Ser | Asn | Leu | Asp | Ser | Cys | Leu | Ile | Ala | Lys | Ala | Gly | Leu | Arg | Val | |
| | | | | 25 | | | | | 30 | | | | | 35 | |
| TAT | TAC | CGG | TGT | TGG | AAG | TTT | GAG | GAT | TGC | ACT | TTC | AGA | CAA | CTT | 225 |
| Tyr | Tyr | Arg | Cys | Trp | Lys | Phe | Glu | Asp | Cys | Thr | Phe | Arg | Gln | Leu | |
| | | | | 40 | | | | | 45 | | | | | 50 | |
| TCA | AAC | CAA | TTG | TCG | GAA | AAT | GAG | TTA | AAG | TAT | CAC | TGC | TGC | AGG | 270 |
| Ser | Asn | Gln | Leu | Ser | Glu | Asn | Glu | Leu | Lys | Tyr | His | Cys | Cys | Arg | |
| | | | | 55 | | | | | 60 | | | | | 65 | |
| GAG | AAC | CTG | TGT | AAC | TTT | AAC | GGA | ATA | CTT | GAA | AAT | GGT | GGG | ACA | 315 |
| Glu | Asn | Leu | Cys | Asn | Phe | Asn | Gly | Ile | Leu | Glu | Asn | Gly | Gly | Thr | |
| | | | | 70 | | | | | 75 | | | | | 80 | |
| ACC | TTA | TCA | AAG | AAA | ACA | GTT | CTT | CTG | CTG | GTG | ACC | CCT | TTT | CTG | 360 |
| Thr | Leu | Ser | Lys | Lys | Thr | Val | Leu | Leu | Leu | Val | Thr | Pro | Phe | Leu | |
| | | | | 85 | | | | | 90 | | | | | 95 | |
| GCA | GCA | GCC | TGG | AGC | CTT | CAT | CCC | TAA | | | | | | | 387 |

Ala Ala Ala Trp Ser Leu His Pro
                100

( 2 ) INFORMATION FOR SEQ ID NO:6:

( i ) SEQUENCE CHARACTERISTICS:
        ( A ) LENGTH: 1039 base pairs
        ( B ) TYPE: Nucleic Acid
        ( C ) STRANDEDNESS: Double
        ( D ) TOPOLOGY: Linear ( i i ) MOLECULE TYPE: cDNA to mRNA
        ( A ) DESCRIPTION: HVS-15 full length cDNA ( i i i ) HYPOTHETICAL: No ( i v ) ANTI-SENSE: No ( v i ) ORIGINAL SOURCE:
        ( A ) ORGANISM: Herpesvirus saimiri ( x ) PUBLICATION INFORMATION:
        ( A ) AUTHORS: Albrecht, J.C.
            Nicholas, J.
            Cameron. K.R.
            Newman, C.
            Fleckenstein, B.
            Honess, R.W.
        ( B ) TITLE: Herpesvirus samiri has a gene specifying
            a homologue of the cellular membrane
            glycoprotein CD59.
        ( C ) JOURNAL: Virology
        ( D ) VOLUME: 190
        ( F ) PAGES: 527-530
        ( G ) DATE: 1992

( x i ) SEQUENCE DESCRIPTION: SEQ ID NO:6:

```
AAGCTTCTAT    TTATACTACA    TTAGAGGCAT    TTTTTCAAAA    GCAAAAATGC                  50

CTCTAATTAT    ATACACTGTA    CTATTTACCT    CTATTACACA    TTTTCTATTT                 100

TAAGTCTGAT    AGTGATTAAT    CAAGAAAAAA    GTTTGTGGTT    CTCAGGGGAT                 150

TAGTTCACAA    GCTGTCTGAG    GTTAAGGGTG    TTTCTTTGGC    ACTGACACAG                 200

AAGTTGCTAT    AAGAATTGAA    GCTTGCTTTA    CAAAAAGTTA    CTTGTGATTA                 250

ATTACTATAA    CAAGAAAGGT    A ATG TAT ATT TTG TTT ACG TTG GTA                      295
                             Met Tyr Ile Leu Phe Thr Leu Val
                                                 - 1 5

CTG ACT TTT GTT TTT TGC AAG CCA ATA CAC AGC TTG CAA TGC                            337
Leu Thr Phe Val Phe Cys Lys Pro Ile His Ser Leu Gln Cys
    - 1 0                   - 5                     1

TAC AAC TGT TCT CAC TCA ACT ATG CAG TGT ACT ACA TCT ACT                            379
Tyr Asn Cys Ser His Ser Thr Met Gln Cys Thr Thr Ser Thr
        5                    1 0                1 5

AGT TGT ACA TCT AAT CTT GAC TCT TGT CTC ATT GCT AAA GCT                            421
Ser Cys Thr Ser Asn Leu Asp Ser Cys Leu Ile Ala Lys Ala
            2 0                  2 5                3 0

GGG TCA GGA GTA TAT TAC AGG TGT TGG AAG TTT GAT GAC TGT                            463
Gly Ser Gly Val Tyr Tyr Arg Cys Trp Lys Phe Asp Asp Cys
                3 5               4 0                    4 5

AGC TTT AAA CGT ATC TCA AAT CAA TTG TCT GAA ACA CAG TTA                            505
Ser Phe Lys Arg Ile Ser Asn Gln Leu Ser Glu Thr Gln Leu
                    5 0               5 5

AAG TAT CAT TGT TGT AAG AAG AAC TTG TGT AAT GTG AAC AAA                            547
Lys Tyr His Cys Cys Lys Lys Asn Leu Cys Asn Val Asn Lys
6 0                  6 5                      7 0

GGG ATT GAA AAT ATT AAA AGA ACA ATA TCA GAT AAA GCT CTT                            589
Gly Ile Glu Asn Ile Lys Arg Thr Ile Ser Asp Lys Ala Leu
        7 5                  8 0                  8 5
```

```
TTA  CTA  TTA  GCA  TTG  TTT  TTA  GTA  ACT  GCT  TGG  AAC  TTT  CCT           631
Leu  Leu  Leu  Ala  Leu  Phe  Leu  Val  Thr  Ala  Trp  Asn  Phe  Pro
          90                       95                      100

CTT  TAAAAG     TCAACAACAA  AACTATATTG  TAACATTTAT  TTTTGTGTAG                  680
Leu

CTTATTTGTA  TTGCTATTAC  AAGTTAAAAT  ATTGTGTTTT  TTAAACTATA                      730

ATTTTTAAAA  AGATAAAATG  AGATGTAGTA  TACTACATAG  TCAAAATTAA                      780

AGTGCTAAAT  ATTATTAGCA  ATTTTTTATC  AACAACGCAA  ATAAAAGTTA                      830

AGCTACTTTA  TTTTTTCTGT  TATCTAAATC  ATTACGCGCT  TCTTAGCATG                      880

TGTTAAAAGT  TTTATGTGAT  TTTATTCTTA  CATATATAAA  GCTAAATTTT                      930

AAAGCAAATT  ATCAGTAGCA  TCTTATCTTC  TAATCTGTAC  AGACCTATAT                      980

AATATGGGAT  TATCCTTAAG  AAAAAACAGC  GGAGAAAAAG  AAAACACAGT                     1030

GCCAAGCTT                                                                      1039
```

(2) INFORMATION FOR SEQ ID NO:7:

(i) SEQUENCE CHARACTERISTICS:
        (A) LENGTH: 1139 base pairs
        (B) TYPE: Nucleic Acid
        (C) STRANDEDNESS: Double
        (D) TOPOLOGY: Linear (ii) MOLECULE TYPE: cDNA to mRNA
        (A) DESCRIPTION: CD59 full length cDNA (iii) HYPOTHETICAL: No (iv) ANTI-SENSE: No (vi) ORIGINAL SOURCE:
        (A) ORGANISM: Homo sapiens (x) PUBLICATION INFORMATION:
        (A) AUTHORS: Philbrick, W.M.
                 Palfree, R.G.E
                 Maher, S.E.
                 Bridgett, M.M.
                 Sirlin S.
                 Bothwell, A.L.M.
        (B) TITLE: The CD59 antigen is a structural
             homologue of murine Ly-6 antigens but
             lacks interferon inducibility.
        (C) JOURNAL: European Journal of Immunology
        (D) VOLUME: 20
        (F) PAGES: 87-92
        (G) DATE: JAN-1990

(xi) SEQUENCE DESCRIPTION: SEQ ID NO:7:

```
CGCAGAAGCG  GCTCGAGGCT  GGAAGAGGAT  CCTGGGCGCC  GCAGGTTCTG                       50

TGGACAATCA  CA  ATG  GGA  ATC  CAA  GGA  GGG  TCT  GTC  CTG  TTC                 92
                Met  Gly  Ile  Gln  Gly  Gly  Ser  Val  Leu  Phe
                -25                      -20

GGG  CTG  CTG  CTC  GTC  CTG  GCT  GTC  TTC  TGC  CAT  TCA  GGT  CAT           134
Gly  Leu  Leu  Leu  Val  Leu  Ala  Val  Phe  Cys  His  Ser  Gly  His
-15                      -10                       -5

AGC  CTG  CAG  TGC  TAC  AAC  TGT  CCT  AAC  CCA  ACT  GCT  GAC  TGC           176
Ser  Leu  Gln  Cys  Tyr  Asn  Cys  Pro  Asn  Pro  Thr  Ala  Asp  Cys
      1                 5                           10

AAA  ACA  GCC  GTC  AAT  TGT  TCA  TCT  GAT  TTT  GAT  GCG  TGT  CTC           218
Lys  Thr  Ala  Val  Asn  Cys  Ser  Ser  Asp  Phe  Asp  Ala  Cys  Leu
      15                      20                       25

ATT  ACC  AAA  GCT  GGG  TTA  CAA  GTG  TAT  AAC  AAG  TGT  TGG  AAG           260
Ile  Thr  Lys  Ala  Gly  Leu  Gln  Val  Tyr  Asn  Lys  Cys  Trp  Lys
```

|  |  |  |  |  |  |  |  |  |  |  |  |  |
|---|---|---|---|---|---|---|---|---|---|---|---|---|
|  | 30 |  |  |  | 35 |  |  |  |  | 40 |  |  |

```
        30                              35                              40
TTT  GAG  CAT  TGC  AAT  TTC  AAC  GAC  GTC  ACA  ACC  CGC  TTG  AGG                    302
Phe  Glu  His  Cys  Asn  Phe  Asn  Asp  Val  Thr  Thr  Arg  Leu  Arg
               45                       50                       55

GAA  AAT  GAG  CTA  ACG  TAC  TAC  TGC  TGC  AAG  AAG  GAC  CTG  TGT                    344
Glu  Asn  Glu  Leu  Thr  Tyr  Tyr  Cys  Cys  Lys  Lys  Asp  Leu  Cys
                    60                       65

AAC  TTT  AAC  GAA  CAG  CTT  GAA  AAT  GGT  GGG  ACA  TCC  TTA  TCA                    386
Asn  Phe  Asn  Glu  Gln  Leu  Glu  Asn  Gly  Gly  Thr  Ser  Leu  Ser
70                       75                       80

GAG  AAA  ACA  GTT  CTT  CTG  CTG  GTG  ACT  CCA  TTT  CTG  GCA  GCA                    428
Glu  Lys  Thr  Val  Leu  Leu  Leu  Val  Thr  Pro  Phe  Leu  Ala  Ala
     85                            90                       95

GCC  TGG  AGC  CTT  CAT  CCC  TAA  G TCAACACCAG  GAGAGCTTCT                              470
Ala  Trp  Ser  Leu  His  Pro
          100
```

| | |
|---|---|
| CCCAAACTCC  CCGTTCCTGC  GTAGTCCGCT  TTCTCTTGCT  GCCACATTCT | 520 |
| AAAGGCTTGA  TATTTTCCAA  ATGGATCCTG  TTGGGAAAGA  ATAAAATTAG | 570 |
| CTTGAGCAAC  CTGGCTAAGA  TAGAGGGGTC  TGGGAGACTT  TGAAGACCAG | 620 |
| TCCTGCCCGC  AGGGAAGCCC  CACTTGAAGG  AAGAAGTCTA  AGAGTGAAGT | 670 |
| AGGTGTGACT  TGAACTAGAT  TGCATGCTTC  CTCCTTTGCT  CTTGGGAAGA | 720 |
| CCAGCTTTGC  AGTGACAGCT  TGAGTGGGTT  CTCTGCAGCC  CTCAGATTAT | 770 |
| TTTTCCTCTG  GCTCCTTGGA  TGTAGTCAGT  TAGCATCATT  AGTACATCTT | 820 |
| TGGAGGGTGG  GGCAGGAGTA  TATGAGCATC  CTCTCTCACA  TGGAACGCTT | 870 |
| TCATAAACTT  CAGGGATCCC  GTGTTGCCAT  GGAGGCATGC  CAAATGTTCC | 920 |
| ATATGTGGGT  GTCAGTCAGG  GACAACAAGA  TCCTTAATGC  AGAGCTAGAG | 970 |
| GACTTCTGGC  AGGGAAGTGG  GGAAGTGTTC  CAGATTCCAG  ATAGCAGGGC | 1020 |
| ATGAAAACTT  AGAGAGGTAC  AAGTGGCTGA  AAATCGAGTT  TTTCCTCTGT | 1070 |
| CTTTAAATTT  TATATGGGCT  TTGTTATCTT  CCACTGGAAA  AGTGTAATAG | 1120 |
| CATACATCAA  TGGTGTGTT | 1139 |

( 2 ) INFORMATION FOR SEQ ID NO:8:

( i ) SEQUENCE CHARACTERISTICS:
        ( A ) LENGTH: 1530 base pairs
        ( B ) TYPE: Nucleic Acid
        ( C ) STRANDEDNESS: Double
        ( D ) TOPOLOGY: Linear ( i i ) MOLECULE TYPE: cDNA to mRNA
        ( A ) DESCRIPTION: MCP (CD46) full length cDNA ( i i i ) HYPOTHETICAL: No ( i v ) ANTI-SENSE: No ( v i ) ORIGINAL SOURCE:
        ( A ) ORGANISM: Homo sapiens ( x ) PUBLICATION INFORMATION:
        ( A ) AUTHORS: Lublin, D.M.
                Liszewski,M.K.
                Post, T.W.
                Arce, M.A.
                LeBeau, M.M.
                Rebentisch, M.B.
                Lemons, R.S.
                Seya, T.
                Atkinson, J.P.
        ( B ) TITLE: Molecular cloning and Chromosomal Localization of Membrane Cofactor
Protein (MCP): Evidence for Inclusion
in the Multi-Gene Family of
Complement- Regulatory Proteins.
( C ) JOURNAL: Journal of Experimental Medicine
( D ) VOLUME: 168
( F ) PAGES: 181-194
( G ) DATE: 1988

( x i ) SEQUENCE DESCRIPTION: SEQ ID NO:8:

| | | | | | | | | | | | | | |
|---|---|---|---|---|---|---|---|---|---|---|---|---|---|
| TCTGCTTTCC | TCCGGAGAAA | TAACAGCGTC | TTCCGCGCCG | CGC | ATG | GAG | | | | | | | 49 |
| | | | | | Met | Glu | | | | | | | |
| CCT | CCC | GGC | CGC | CGC | GAG | TGT | CCC | TTT | CCT | TCC | TGG | CGC | TTT | 91 |
| Pro | Pro | Gly | Arg | Arg | Glu | Cys | Pro | Phe | Pro | Ser | Trp | Arg | Phe |
| | | -30 | | | | -25 | | | | | -20 | | |
| CCT | GGG | TTG | CTT | CTG | GCG | GCC | ATG | GTG | TTG | CTG | CTG | TAC | TCC | 133 |
| Pro | Gly | Leu | Leu | Leu | Ala | Ala | Met | Val | Leu | Leu | Leu | Tyr | Ser |
| | | | -15 | | | | -10 | | | | | | -5 |
| TTC | TCC | GAT | GCC | TGT | GAG | GAG | CCA | CCA | ACA | TTT | GAA | GCT | ATG | 175 |
| Phe | Ser | Asp | Ala | Cys | Glu | Glu | Pro | Pro | Thr | Phe | Glu | Ala | Met |
| | | | | 1 | | | | 5 | | | | | 10 |
| GAG | CTC | ATT | GGT | AAA | CCA | AAA | CCC | TAC | TAT | GAG | ATT | GGT | GAA | 217 |
| Glu | Leu | Ile | Gly | Lys | Pro | Lys | Pro | Tyr | Tyr | Glu | Ile | Gly | Glu |
| | | | | 15 | | | | | 20 | | | | |
| CGA | GTA | GAT | TAT | AAG | TGT | AAA | AAA | GGA | TAC | TTC | TAT | ATA | CCT | 259 |
| Arg | Val | Asp | Tyr | Lys | Cys | Lys | Lys | Gly | Tyr | Phe | Tyr | Ile | Pro |
| 25 | | | | | 30 | | | | | 35 | | | |
| CCT | CTT | GCC | ACC | CAT | ACT | ATT | TGT | GAT | CGG | AAT | CAT | ACA | TGG | 301 |
| Pro | Leu | Ala | Thr | His | Thr | Ile | Cys | Asp | Arg | Asn | His | Thr | Trp |
| | | 40 | | | | 45 | | | | | 50 | | |
| CTA | CCT | GTC | TCA | GAT | GAC | GCC | TGT | TAT | AGA | GAA | ACA | TGT | CCA | 343 |
| Leu | Pro | Val | Ser | Asp | Asp | Ala | Cys | Tyr | Arg | Glu | Thr | Cys | Pro |
| | | 55 | | | | | 60 | | | | | 65 | |
| TAT | ATA | CGG | GAT | CCT | TTA | AAT | GGC | CAA | GCA | GTC | CCT | GCA | AAT | 385 |
| Tyr | Ile | Arg | Asp | Pro | Leu | Asn | Gly | Gln | Ala | Val | Pro | Ala | Asn |
| | | | 70 | | | | | 75 | | | | | 80 |
| GGG | ACT | TAC | GAG | TTT | GGT | TAT | CAG | ATG | CAC | TTT | ATT | TGT | AAT | 427 |
| Gly | Thr | Tyr | Glu | Phe | Gly | Tyr | Gln | Met | His | Phe | Ile | Cys | Asn |
| | | | | 85 | | | | | 90 | | | | |
| GAG | GGT | TAT | TAC | TTA | ATT | GGT | GAA | GAA | ATT | CTA | TAT | TGT | GAA | 469 |
| Glu | Gly | Tyr | Tyr | Leu | Ile | Gly | Glu | Glu | Ile | Leu | Tyr | Cys | Glu |
| 95 | | | | | 100 | | | | | 105 | | | |
| CTT | AAA | GGA | TCA | GTA | GCA | ATT | TGG | AGC | GGT | AAG | CCC | CCA | ATA | 511 |
| Leu | Lys | Gly | Ser | Val | Ala | Ile | Trp | Ser | Gly | Lys | Pro | Pro | Ile |
| | 110 | | | | | 115 | | | | | 120 | | |
| TGT | GAA | AAG | GTT | TTG | TGT | ACA | CCA | CCT | CCA | AAA | ATA | AAA | AAT | 553 |
| Cys | Glu | Lys | Val | Leu | Cys | Thr | Pro | Pro | Pro | Lys | Ile | Lys | Asn |
| | | 125 | | | | | 130 | | | | | 135 | |
| GGA | AAA | CAC | ACC | TTT | AGT | GAA | GTA | GAA | GTA | TTT | GAG | TAT | CTT | 595 |
| Gly | Lys | His | Thr | Phe | Ser | Glu | Val | Glu | Val | Phe | Glu | Tyr | Leu |
| | | | 140 | | | | | 145 | | | | | 150 |
| GAT | GCA | GTA | ACT | TAT | AGT | TGT | GAT | CCT | GCA | CCT | GGA | CCA | GAT | 637 |
| Asp | Ala | Val | Thr | Tyr | Ser | Cys | Asp | Pro | Ala | Pro | Gly | Pro | Asp |
| | | | | 155 | | | | | 160 | | | | |
| CCA | TTT | TCA | CTT | ATT | GGA | GAG | AGC | ACG | ATT | TAT | TGT | GGT | GAC | 679 |
| Pro | Phe | Ser | Leu | Ile | Gly | Glu | Ser | Thr | Ile | Tyr | Cys | Gly | Asp |
| 165 | | | | | 170 | | | | | 175 | | | |
| AAT | TCA | GTG | TGG | AGT | CGT | GCT | GCT | CCA | GAG | TGT | AAA | GTG | GTC | 721 |
| Asn | Ser | Val | Trp | Ser | Arg | Ala | Ala | Pro | Glu | Cys | Lys | Val | Val |
| | | 180 | | | | | 185 | | | | | 190 | |
| AAA | TGT | CGA | TTT | CCA | GTA | GTC | GAA | AAT | GGA | AAA | CAG | ATA | TCA | 763 |
| Lys | Cys | Arg | Phe | Pro | Val | Val | Glu | Asn | Gly | Lys | Gln | Ile | Ser |

|     |     |     |     |     |     |     |     |     |     |     |     |     |      |
|-----|-----|-----|-----|-----|-----|-----|-----|-----|-----|-----|-----|-----|------|
| GGA | TTT | GGA | AAA | AAA | TTT | TAC | TAC | AAA | GCA | ACA | GTT | ATG | TTT  | 805 |
| Gly | Phe | Gly | Lys | Lys | Phe | Tyr | Tyr | Lys | Ala | Thr | Val | Met | Phe  |
|     |     |     | 210 |     |     |     |     | 215 |     |     |     |     | 220  |
| GAA | TGC | GAT | AAG | GGT | TTT | TAC | CTC | GAT | GGC | AGC | GAC | ACA | ATT  | 847 |
| Glu | Cys | Asp | Lys | Gly | Phe | Tyr | Leu | Asp | Gly | Ser | Asp | Thr | Ile  |
|     |     |     |     | 225 |     |     |     |     | 230 |     |     |     |      |
| GTC | TGT | GAC | AGT | AAC | AGT | ACT | TGG | GAT | CCC | CCA | GTT | CCA | AAG  | 889 |
| Val | Cys | Asp | Ser | Asn | Ser | Thr | Trp | Asp | Pro | Pro | Val | Pro | Lys  |
| 235 |     |     |     |     | 240 |     |     |     |     | 245 |     |     |      |
| TGT | CTT | AAA | GTG | TCG | ACT | TCT | TCC | ACT | ACA | AAA | TCT | CCA | GCG  | 931 |
| Cys | Leu | Lys | Val | Ser | Thr | Ser | Ser | Thr | Thr | Lys | Ser | Pro | Ala  |
|     | 250 |     |     |     |     | 255 |     |     |     |     | 260 |     |      |
| TCC | AGT | GCC | TCA | GGT | CCT | AGG | CCT | ACT | TAC | AAG | CCT | CCA | GTC  | 973 |
| Ser | Ser | Ala | Ser | Gly | Pro | Arg | Pro | Thr | Tyr | Lys | Pro | Pro | Val  |
|     |     | 265 |     |     |     |     | 270 |     |     |     |     | 275 |      |
| TCA | AAT | TAT | CCA | GGA | TAT | CCT | AAA | CCT | GAG | GAA | GGA | ATA | CTT  | 1015 |
| Ser | Asn | Tyr | Pro | Gly | Tyr | Pro | Lys | Pro | Glu | Glu | Gly | Ile | Leu  |
|     |     |     | 280 |     |     |     |     | 285 |     |     |     |     | 290  |
| GAC | AGT | TTG | GAT | GTT | TGG | GTC | ATT | GCT | GTG | ATT | GTT | ATT | GCC  | 1057 |
| Asp | Ser | Leu | Asp | Val | Trp | Val | Ile | Ala | Val | Ile | Val | Ile | Ala  |
|     |     |     |     | 295 |     |     |     |     | 300 |     |     |     |      |
| ATA | GTT | GTT | GGA | GTT | GCA | GTA | ATT | TGT | GTT | GTC | CCG | TAC | AGA  | 1099 |
| Ile | Val | Val | Gly | Val | Ala | Val | Ile | Cys | Val | Val | Pro | Tyr | Arg  |
| 305 |     |     |     |     | 310 |     |     |     |     | 315 |     |     |      |
| TAT | CTT | CAA | AGG | AGG | AAG | AAG | AAA | GGG | AAA | GCA | GAT | GGT | GGA  | 1141 |
| Tyr | Leu | Gln | Arg | Arg | Lys | Lys | Lys | Gly | Lys | Ala | Asp | Gly | Gly  |
|     | 320 |     |     |     |     | 325 |     |     |     |     | 330 |     |      |
| GCT | GAA | TAT | GCC | ACT | TAC | CAG | ACT | AAA | TCA | ACC | ACT | CCA | GCA  | 1183 |
| Ala | Glu | Tyr | Ala | Thr | Tyr | Gln | Thr | Lys | Ser | Thr | Thr | Pro | Ala  |
|     |     | 335 |     |     |     |     | 340 |     |     |     |     | 345 |      |

| GAG | CAG | AGA | GGC | TGA | AT AGATTCCACA ACCTGGTTTG CCAGTTCATC | 1230 |
|-----|-----|-----|-----|-----|------|------|
| Glu | Gln | Arg | Gly |     |      |
|     |     |     | 350 |     |      |

| TTTTGACTCT | ATTAAAATCT | TCAATAGTTG | TTATTCTGTA | GTTTCACTCT | 1280 |
| CATGAGTGCA | ACTGTGGCTT | AGCTAATATT | GCAATGTGGC | TTGAATGTAG | 1330 |
| GTAGCATCCT | TTGATGCTTC | TTTGAAACTT | GTATGAATTT | GGGTATGAAC | 1380 |
| AGATTGCCTG | CTTTCCCTTA | AATAACACTT | AGATTTATTG | GACCAGTCAG | 1430 |
| CACAGCATGC | CTGGTTGTAT | TAAAGCAGGG | ATATGCTGTA | TTTTATAAAA | 1480 |
| TTGGCAAAAT | TAGAGAAATA | TAGTTCACAA | TGAAATTATA | TTTTCTTTGT | 1530 |

(2) INFORMATION FOR SEQ ID NO:9:

(i) SEQUENCE CHARACTERISTICS:
        (A) LENGTH: 26 bases
        (B) TYPE: Nucleic Acid
        (C) STRANDEDNESS: Single
        (D) TOPOLOGY: Linear (ii) MOLECULE TYPE: Other nucleic acid (iii) HYPOTHETICAL: No (iv) ANTI-SENSE: No (xi) SEQUENCE DESCRIPTION: SEQ ID NO:9:
        CGCGAGGCCT ACTTACAAGC CTCCAG (2) INFORMATION FOR SEQ ID NO:10:

(i) SEQUENCE CHARACTERISTICS:
        (A) LENGTH: 26 bases (B) TYPE: Nucleic Acid
(C) STRANDEDNESS: Single
(D) TOPOLOGY: Linear (ii) MOLECULE TYPE: Other nucleic acid (iii) HYPOTHETICAL: No (iv) ANTI-SENSE: Yes (xi) SEQUENCE DESCRIPTION: SEQ ID NO:10:

CGCGCTATTC AGCCTCTCTG CTCTGC (2) INFORMATION FOR SEQ ID NO:11:

(i) SEQUENCE CHARACTERISTICS:
(A) LENGTH: 261 base pairs
(B) TYPE: Nucleic Acid
(C) STRANDEDNESS: Double
(D) TOPOLOGY: Linear (ii) MOLECULE TYPE: Other nucleic acid
(A) DESCRIPTION: MCP PCR Product (iii) HYPOTHETICAL: No (iv) ANTI-SENSE: No (xi) SEQUENCE DESCRIPTION: SEQ ID NO:11:

| | | | | | |
|---|---|---|---|---|---|
| CGCGAGGCCT | ACTTACAAGC | CTCCAGTCTC | AAATTATCCA | GGATATCCTA | 50 |
| AACCTGAGGA | AGGAATACTT | GACAGTTTGG | ATGTTTGGGT | CATTGCTGTG | 100 |
| ATTGTTATTG | CCATAGTTGT | TGGAGTTGCA | GTAATTTGTG | TTGTCCCGTA | 150 |
| CAGATATCTT | CAAAGGAGGA | AGAAGAAAGG | GAAAGCAGAT | GGTGGAGCTG | 200 |
| AATATGCCAC | TTACCAGACT | AAATCAACCA | CTCCAGCAGA | GCAGAGAGGC | 250 |
| TGAATAGCGC | G | | | | 261 |

(2) INFORMATION FOR SEQ ID NO:12:

(i) SEQUENCE CHARACTERISTICS:
(A) LENGTH: 69 bases
(B) TYPE: Nucleic Acid
(C) STRANDEDNESS: Single
(D) TOPOLOGY: Linear (ii) MOLECULE TYPE: Other nucleic acid (iii) HYPOTHETICAL: No (iv) ANTI-SENSE: No (xi) SEQUENCE DESCRIPTION: SEQ ID NO:12:

CCGGACCTGT GTAACTTTAA CGAACAGCTT GAAAATATTG GTAGGATATG     50

CAATGGAAAT TGTTACAAC (2) INFORMATION FOR SEQ ID NO:13:

(i) SEQUENCE CHARACTERISTICS:
(A) LENGTH: 20 bases
(B) TYPE: Nucleic Acid
(C) STRANDEDNESS: Single
(D) TOPOLOGY: Linear (ii) MOLECULE TYPE: Other nucleic acid (iii) HYPOTHETICAL: No (iv) ANTI-SENSE: Yes (xi) SEQUENCE DESCRIPTION: SEQ ID NO:13:

TAGTTACTGC CCGGACATGC                                                                                                    20

( 2 ) INFORMATION FOR SEQ ID NO:14:

( i ) SEQUENCE CHARACTERISTICS:
        ( A ) LENGTH: 264 base pairs
        ( B ) TYPE: Nucleic Acid
        ( C ) STRANDEDNESS: Double
        ( D ) TOPOLOGY: Linear ( i i ) MOLECULE TYPE: Other nucleic acid
        ( A ) DESCRIPTION: CCPH PCR Product ( i i i ) HYPOTHETICAL: No ( i v ) ANTI-SENSE: No ( x i ) SEQUENCE DESCRIPTION: SEQ ID NO:14:

CCGGACCTGT GTAACTTTAA CGAACAGCTT GAAAATATTG GTAGGATATG                                                                    50

CAATGGAAAT TGTACAACTA GCATGCCCAC TCAAACATAT ACAATAATTA                                                                   100

CTGCGCGCTA TACAAGTCAC ATATATTTCC CTACTGGGAA AACCTATAAA                                                                   150

CTTCCTCGGG GAGTTCTAGT AATTATTCTT ACCACAAGCT TTATTATTAT                                                                   200

TGGAATAATA CTTACTGGAG TGTGTTTACA TAGGTGCAGA GTGTGCATGT                                                                   250

CCGGGCAGTA ACTA                                                                                                          264

( 2 ) INFORMATION FOR SEQ ID NO:15:

( i ) SEQUENCE CHARACTERISTICS:
        ( A ) LENGTH: 70 amino acids
        ( B ) TYPE: Amino Acid
        ( C ) STRANDEDNESS: Single
        ( D ) TOPOLOGY: Linear ( i x ) FEATURE:
        ( D ) OTHER INFORMATION: amino acid residues
            11, 12, and 13 are optional and one, two, or three of
            them may be deleted ( x i ) SEQUENCE DESCRIPTION: SEQ ID NO:15:

Cys Xaa Xaa Cys Xaa Xaa Xaa Xaa Xaa Xaa Xaa Xaa Xaa Cys Xaa
               5                         10                    15

Xaa Xaa Xaa Xaa Cys Xaa Xaa Xaa Xaa Xaa Xaa Cys Xaa Xaa Xaa
              20                     25                   30

Xaa Xaa Xaa Xaa Xaa Xaa Xaa Xaa Xaa Cys Xaa Xaa Xaa Xaa Xaa
                 35                   40                   45

Cys Xaa Xaa Xaa Xaa Xaa Xaa Xaa Xaa Xaa Xaa Xaa Xaa Xaa Xaa
              50                     55                   60

Xaa Xaa Xaa Cys Cys Xaa Xaa Xaa Xaa Cys
            65                     70

( 2 ) INFORMATION FOR SEQ ID NO:16:

( i ) SEQUENCE CHARACTERISTICS:
        ( A ) LENGTH: 70 amino acids
        ( B ) TYPE: Amino Acid
        ( C ) STRANDEDNESS: Single
        ( D ) TOPOLOGY: Linear ( i x ) FEATURE:
        ( D ) OTHER INFORMATION: amino acid residues
            11, 12, and 13 are optional and one, two, or three of
            them may be deleted; residue 26 is Thr or Ser, residue
            39 is Gln or Arg, residue 45 is Asn or Asp ( x i ) SEQUENCE DESCRIPTION: SEQ ID NO:16:

-continued

| Cys | Xaa | Xaa | Cys | Pro   | Xaa | Xaa | Xaa | Xaa | Xaa   | Xaa | Xaa | Xaa | Cys | Xaa   |
|-----|-----|-----|-----|-------|-----|-----|-----|-----|-------|-----|-----|-----|-----|-------|
|     |     |     |     | 5     |     |     |     |     | 1 0   |     |     |     |     | 1 5   |
| Xaa | Xaa | Xaa | Asn | Cys   | Xaa | Xaa | Xaa | Xaa | Xaa   | Xaa | Cys | Xaa | Xaa | Xaa   |
|     |     |     |     | 2 0   |     |     |     |     | 2 5   |     |     |     |     | 3 0   |
| Xaa | Xaa | Xaa | Xaa | Xaa   | Xaa | Xaa | Xaa | Xaa | Cys   | Xaa | Xaa | Xaa | Xaa | Xaa   |
|     |     |     |     | 3 5   |     |     |     |     | 4 0   |     |     |     |     | 4 5   |
| Cys | Xaa | Xaa | Xaa | Xaa   | Xaa | Xaa | Xaa | Xaa | Xaa   | Xaa | Xaa | Xaa | Xaa | Xaa   |
|     |     |     |     | 5 0   |     |     |     |     | 5 5   |     |     |     |     | 6 0   |
| Xaa | Xaa | Xaa | Cys | Cys   | Xaa | Xaa | Xaa | Xaa | Cys   |     |     |     |     |       |
|     |     |     |     | 6 5   |     |     |     |     | 7 0   |     |     |     |     |       |

( 2 ) INFORMATION FOR SEQ ID NO:17:

( i ) SEQUENCE CHARACTERISTICS:
        ( A ) LENGTH: 29 amino acids
        ( B ) TYPE: Amino Acid
        ( C ) STRANDEDNESS: Single
        ( D ) TOPOLOGY: Linear ( i x ) FEATURE:
        ( D ) OTHER INFORMATION: all Xaa amino acid residues
            are limited to two or three possible amino acids (which
            may differ in each case) as disclosed under heading
            " DESCRIPTION OF THE PREFERRED EMBODIMENTS", subheading
            " Terminal CIPs"

( x i ) SEQUENCE DESCRIPTION: SEQ ID NO:17:

| Xaa | Xaa | Asn | Xaa | Xaa  | Xaa | Xaa | Xaa | Ser | Xaa   | Lys | Xaa | Xaa | Xaa | Leu   |
|-----|-----|-----|-----|------|-----|-----|-----|-----|-------|-----|-----|-----|-----|-------|
|     |     |     |     | 5    |     |     |     |     | 1 0   |     |     |     |     | 1 5   |
| Leu | Xaa | Xaa | Xaa | Xaa  | Leu | Xaa | Xaa | Ala | Trp   | Xaa | Xaa | Xaa | Xaa |       |
|     |     |     |     | 2 0  |     |     |     |     | 2 5   |     |     |     |     |       |